(12) United States Patent
Agah et al.

(10) Patent No.: US 12,064,614 B2
(45) Date of Patent: *Aug. 20, 2024

(54) METHODS AND SYSTEMS FOR DEPLOYMENT, CHARGING AND RETRIEVAL OF INTRACARDIAC PUMPS

(71) Applicant: Ramtin Agah, Menlo Park, CA (US)

(72) Inventors: Ramtin Agah, Menlo Park, CA (US); Kamran Najmabadi, Palo Alto, CA (US); Alex Alden Peterson, Ottertail, MN (US)

(73) Assignee: Ramtin Agah, Menlo Park, CA (US)

( * ) Notice: Subject to any disclaimer, the term of this patent is extended or adjusted under 35 U.S.C. 154(b) by 671 days.

This patent is subject to a terminal disclaimer.

(21) Appl. No.: 17/328,363

(22) Filed: May 24, 2021

(65) Prior Publication Data

US 2021/0275795 A1    Sep. 9, 2021

Related U.S. Application Data

(63) Continuation-in-part of application No. 16/087,079, filed as application No. PCT/US2017/023348 on Mar. 21, 2017, now Pat. No. 11,406,812.

(Continued)

(51) Int. Cl.
*A61M 60/165* (2021.01)
*A61M 60/139* (2021.01)
*A61M 60/295* (2021.01)

(52) U.S. Cl.
CPC ........ *A61M 60/165* (2021.01); *A61M 60/139* (2021.01); *A61M 60/295* (2021.01);
(Continued)

(58) Field of Classification Search
CPC .............. A61M 60/135; A61M 60/148; A61M 60/205; A61M 60/422; A61M 1/3653;
(Continued)

(56) References Cited

U.S. PATENT DOCUMENTS

| 5,911,685 A | 6/1999 | Siess et al. |
| 6,530,876 B1 | 3/2003 | Spence |

(Continued)

FOREIGN PATENT DOCUMENTS

| EP | 0894505 B1 | 12/2006 |
| WO | 2009091965 A1 | 7/2009 |

(Continued)

OTHER PUBLICATIONS

El Feghaly et al., article entitled 'Endovascular retrieval of two migrated venous stents by means of balloon catheters,' Journal of Vascular Surgery, vol. 28, No. 3, p. 541-546, Sep. 1998.

(Continued)

*Primary Examiner* — Jon Eric C Morales

(74) *Attorney, Agent, or Firm* — Shay Glenn LLP

(57) ABSTRACT

An apparatus includes a stent configured to releasably support a blood pump within an inner lumen of the stent. The stent can include one or more arms configured to bend radially inward and releasably couple to attachment portions on a housing of the blood pump. The attachment portions of the blood pump housing may include one or more slotted openings for accepting the arms extending from the stent. A magnetic member may assist in coupling the arms to the blood pump housing. When decoupling the blood pump from the stent, a position of the blood pump may be adjusted relative to the stent to cause the arms to be released from the attachment portions. Once released, the arms may bend radially outward in alignment with a diameter of the stent.

31 Claims, 30 Drawing Sheets

Related U.S. Application Data

(60) Provisional application No. 62/310,981, filed on Mar. 21, 2016.

(52) U.S. Cl.
CPC ............... *A61M 2205/0266* (2013.01); *A61M 2205/8206* (2013.01)

(58) Field of Classification Search
CPC ........ A61M 1/3659; A61M 2205/8206; A61M 2210/127; A61M 60/414; A61M 60/419; A61F 2/2475; A61F 2220/0016; A61F 2/86; A61F 2002/8486; A61B 5/6862; A61B 5/6876; A61B 5/6882
See application file for complete search history.

(56) References Cited

U.S. PATENT DOCUMENTS

| | | | |
|---|---|---|---|
| 6,911,041 | B1 | 6/2005 | Zscheeg |
| 7,144,364 | B2 | 12/2006 | Barbut et al. |
| 7,479,102 | B2 | 1/2009 | Jarvik |
| 8,562,509 | B2 | 10/2013 | Bates |
| 8,690,749 | B1 | 4/2014 | Nunez |
| 8,840,539 | B2 | 9/2014 | Zilbershlag |
| 9,211,368 | B2 | 12/2015 | Wampler |
| 9,276,641 | B2 | 3/2016 | Hur et al. |
| 9,463,268 | B2 | 10/2016 | Spence |
| 9,561,314 | B2 | 2/2017 | Aboul-Hosn et al. |
| 9,585,991 | B2 | 3/2017 | Spence |
| 11,406,812 | B2 * | 8/2022 | Agah ................. A61M 60/873 |
| 2006/0036127 | A1 | 2/2006 | Delgado, III |
| 2009/0112312 | A1 | 4/2009 | Larose et al. |
| 2010/0191035 | A1 | 7/2010 | Kang et al. |
| 2010/0249489 | A1 | 9/2010 | Jarvik |
| 2012/0283820 | A1 | 11/2012 | Tseng et al. |
| 2013/0138205 | A1 | 5/2013 | Kushwaha et al. |
| 2014/0051908 | A1 | 2/2014 | Khanal et al. |
| 2014/0128659 | A1 | 5/2014 | Heuring et al. |
| 2015/0038770 | A1 | 2/2015 | Colella |
| 2015/0119633 | A1 | 4/2015 | Haselby et al. |
| 2016/0064952 | A1 | 3/2016 | Matsumoto et al. |
| 2020/0324033 | A1 | 10/2020 | Agah et al. |

FOREIGN PATENT DOCUMENTS

| | | |
|---|---|---|
| WO | 2014179391 A2 | 11/2014 |
| WO | 2015130768 A2 | 9/2015 |

OTHER PUBLICATIONS

Feezor et al., article entitled 'Duodenal performation with an inferior vena cava filter: An unusual cause of abdominal pain,' Journal of Vascular Surgery, p. 1-3.

Mukku et al., article entitled 'Use of Impella Ventricular Assist Device in Patients with Severe Coronary Artery Disease Presenting with Cardiac Arrest,' International Journal of Angiology, vol. 21, No. Mar. 2012, p. 163-166, Aug. 20, 2012.

Terry-Cobo, article entitled 'VADovations develops blood pump,' i2E Innovation to Enterprise, May 16, 2013, Retrieved online at: https://i2e.org/vadovations-develops-blood-pump/.

Tsiouris et al., article entitled 'Short and long term outcomes of 200 patients supported by continuous-flow left ventricular assist devices,' World Journal of Cardiology, vol. 7, issue 11, p. 792-800, Nov. 26, 2015, Baishideng Publishing Group Inc., California.

* cited by examiner

- 40

42 — Insert into an entry blood vessel a blood pump assembly, the blood pump assembly including a blood pump, an expandable member, and a plurality of struts. The expandable member including a set of flexible segments that form a tubular wall defining an interior volume, the expandable member including a set of attachment portions. A first end portion of each strut coupled to the blood pump, a second end portion of each strut removably coupled to a corresponding attachment portion such that at least a portion of the blood pump is within the interior volume of the expandable member, the inserting performed when the expandable member is in a collapsed configuration 44 — Advance the blood pump assembly through the entry blood vessel and to a target blood vessel;

46 — Transition the expandable member from the collapsed configuration to an expanded configuration such that the flexible segments contact an inner surface of the target blood vessel and the blood pump is suspended within the target blood vessel by the struts, the blood pump and the struts configured to be removed from the target blood vessel by removing the second end portion of each strut from the plurality of struts from the corresponding attachment portion 48 — Optionally, remove the second end portion of each strut from the corresponding attachment portion when the expandable member is in its expanded configuration within the target blood vessel 49 — Optionally, retrieve the blood pump and the plurality of struts from the target blood vessel

FIG. 19

METHODS AND SYSTEMS FOR DEPLOYMENT, CHARGING AND RETRIEVAL OF INTRACARDIAC PUMPS

CROSS REFERENCE TO RELATED APPLICATIONS

This application is a continuation-in-part of U.S. patent application Ser. No. 16/087,079, filed on Mar. 21, 2017, published as U.S. Patent Publication No. 2020/0324033 A1, entitled "METHODS AND SYSTEMS FOR DEPLOYMENT, CHARGING AND RETRIEVAL OF INTRACARDIAC PUMPS," which is a National Stage Entry of International Patent Application No. PCT/US2017/023348, having an international filing date of Mar. 21, 2017, published as WO 2017/165372 A1, and claims the benefit of priority to U.S. Provisional Application No. 62/310,981, filed on Mar. 21, 2016, entitled "INTRACARDIAC PUMP AND METHODS FOR DEPLOYMENT AND CHARGING," each of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

The embodiments described herein relate to circulatory support systems and methods. More particularly, the embodiments described herein relate to ventricular assist devices that can be implanted and removed using endovascular procedures.

Known mechanical devices, such as left ventricle assist devices ("LVAD") or intra-aortic balloon pumps ("IABP") can be used to supplement the heart's pumping ability. LVADs are surgically implanted into the chest cavity and provide blood flow from left ventricle of the heart to the aorta. LVADs are often implanted in patients waiting for a heart transplant or as a temporary means to assist the patient in recovering from a temporary heart failure. In some instances, LVADs are implanted as a long-term solution for patients that are not eligible for a heart transplant. IABPs are catheter-based devices with a balloon that inflates inside the aorta when the aortic value is closed (i.e., during diastole) to force blood further into the circulatory system. These devices provide a temporary augmentation of the heart function via a balloon/pump internally connected to the driver outside the body via a catheter.

Although such circulatory-assist devices can effectively supplement the output of the heart, they are not without significant risks. For example, known methods for implanting LVADs require invasive surgical procedures. Specifically, some known methods of implanting LVADs involve open heart surgery (e.g., a midline sternotomy of the chest and utilization of cardiopulmonary bypass). Known methods of implanting circulatory assist devices often include surgical incisions into the heart, which may further weaken the heart. Moreover, because patients in need of a circulatory assist device are usually suffering from chronic congestive heart failure, they are often even more susceptible to complications during and after surgery. Accordingly, the survival rate for LVAD patients one year after implantation is only about 78 percent (Tsiouris et al., "Short and Long Term Outcomes of 200 Patients Supported by Continuous-Flow Left Ventricular Assist Devices," World J. Cardiology, Nov. 26, 2015).

In addition to surgical risks, known circulatory-assist devices include components, such as the pump, that are implanted within the patient's body, and components, such as the controller and power source, that remain outside of the patient's body. The internal and external components are connected using electrical leads or a "driveline" that extends from inside of the body to the external power supply. Such connections are susceptible to infection and can further complicate the use of LVADs as a long-term solution.

To reduce the surgical risks associated with circulatory-assist devices and LVADs, there have been some attempts made to deliver pumps endovascularly, but these also have significant disadvantages. For example, because of the difficulty in traversing the aortic arch, some known procedures including implanting a pump in the descending aorta. Including the inflow cannula downstream of the aortic arch, however, minimizes the effects of the circulatory-assist system on the caudal regions of the patient.

Some known designs and methods include placing a pump within a cage, for example, a structure similar to a vena cava filter, and advancing the pump into the ascending aorta. Such methods, however, employ cages having "hooks" or other single points of attachment to the vessel wall. Accordingly, such systems are susceptible to downstream migration, tipping, and perforating the vessel walls (see, e.g., Feczor et al., "Duodenal Perforation with an Inferior Vena Cava Filter: An Unusual Cause of Abdominal Pain," J. Vascular Surgery, 2002). Moreover, the added weight of suspending a pump within such systems will likely exacerbate such issues.

Moreover, there are no effective techniques for the removal of such implanted pumps using endovascular procedures. For example, the likelihood of effective removal of system that includes a hook or anchor point in direct contact with the vessel wall can decrease with time. Specifically, support systems in direct contact can be subject to endothelialization of the anchor points, which increases the risk of perforating the vessel wall during removal.

Thus, a need exists for improved intracardiac pump assemblies and methods for implantation and removal of intracardiac pump assemblies using endovascular procedures.

SUMMARY OF THE DISCLOSURE

Intracardiac pump assemblies and methods for their implantation and removal are described herein. In some embodiments, an apparatus includes an expandable member, a blood pump, and a set of struts. The expandable member is configured to transition from a collapsed configuration to an expanded configuration. The expandable member includes a set of flexible segments that form a tubular wall defining an interior volume. The flexible segments contact an inner surface of a blood vessel when the expandable member is in the expanded position. The expandable member includes a set of attachment portions. Each of the struts has a first end portion coupled to a housing of the blood pump. Each of the struts has a second end portion configured to be removably coupled to a corresponding attachment portion such that the blood pump can be removably coupled to the expandable member with at least a portion of the housing disposed within the interior volume of the expandable member.

According to some aspects, a blood pump assembly includes a blood pump including a housing having one or more attachment portions (also referred to as attachment sites); a stent configured to transition from a collapsed configuration to an expanded configuration, the stent including a plurality of flexible segments that form a tubular wall defining an interior volume; and one or more arms fixedly coupled to the stent, the one or more arms configured to removable couple to the one or more attachment portions of the blood pump to support the blood pump within the interior volume of the stent, where the one or more arms are configured to detach from the one or more attachment portions such that the blood pump is decoupled from the stent and is removable from the interior volume of the stent.

The one or more attachment portions of the housing of the blood pump may include one or more slotted openings configured to capture one or more attachment features (e.g., attachment members) at distal ends of the one or more arms. The housing may include a magnetic material that is configured to magnetically couple with the one or more attachment members to retain the one or more arms within the one or more slotted openings. The blood pump housing may include a retention member associated with each of the one or more slotted openings, the retention member having a notch configured to accept a corresponding attachment member. The one or more arms may be configured to bend radially inward with respect to the tubular wall of the stent to couple with the blood pump and support the blood pump within the interior volume of the stent. The one or more arms may be configured to bend radially outward and form part of the tubular wall of the stent when detached from the blood pump. The one or more arms may be made of a shape memory material having a pre-deformed shape that is in radial alignment with the tubular wall of the stent. The one or more arms may be configured to detach from the one or more attachment portions upon translation of the blood pump with respect to the stent. Upon translation, the one or more arms may be configured to move radially outward and in alignment with the tubular wall of the stent. The blood pump may include a power supply configured to drive the blood pump. The blood pump assembly further may include a second stent configured to support the power supply within an interior volume of the second stent, where the second stent may include a second set of one or more arms fixedly coupled to the second stent, and where the second set of one or more arms is configured to removably couple to a housing of the power supply. The power supply may be electrically coupled to the blood pump by an electrical lead wire.

According to some aspects, a method of implanting a blood pump assembly includes: advancing the blood pump assembly through an entry blood vessel and to a target blood vessel, the blood pump assembly including: a blood pump (e.g., blood pump component) including a housing having one or more attachment portions; and a stent including a plurality of flexible segments, the stent including one or more arms fixedly coupled thereto, the one or more arms detachably coupled to the one or more attachment portions of the blood pump. The method also may include expanding the stent within the target blood vessel such that the flexible segments contact an inner surface of the target blood vessel and form a tubular wall defining an interior volume, where the one or more arms support the blood pump within the interior volume of the stent.

The method may include percutaneously inserting a catheter containing the blood pump assembly while in a collapsed configuration into the entry blood vessel. The entry blood vessel may be a femoral artery, and the target blood vessel may be an ascending aorta. One or more attachment members (also referred to herein as attachment features) at distal ends of the one or more arms may be captured within one or more slotted openings of the housing of the blood pump. Each of the one or more attachment members may be magnetically retained within a corresponding slotted opening by a magnetic material within the housing. Each of the one or more attachment members may be retained within a corresponding slotted opening by a retention member having a notch configured to accept the attachment member. The one or more arms may be bent radially inward with respect to the tubular wall of the stent to couple with the blood pump and support the blood pump within the interior volume of the stent. The blood pump assembly may include a blood pump and a separate power supply, where expanding the stent may include: expanding a first stent within the target blood vessel such that a first set of arms of the first stent supports the blood pump within an interior volume of the first stent, where the first set of arms is detachably coupled to first attachment portions of a housing of the blood pump; and expanding a second stent within the target blood vessel such that a second set of arms of the second stent supports the power supply within an interior volume of the second stent, where the second set of arms is detachably coupled to second attachment portions of a housing of the power supply. The power supply may be electrically coupled to the blood pump by an electrical lead wire.

According to some aspects, a method of removing a blood pump from blood pump assembly implanted within a blood vessel includes: advancing a retrieval sheath through the blood vessel toward the blood pump assembly, the blood pump assembly includes: the blood pump including a housing having one or more attachment portions; and a stent including a plurality of flexible segments contacting an inner surface of the blood vessel and forming a tubular wall defining an interior volume, the stent including one or more arms fixedly coupled to the stent, the one or more arms extending radially inward within the interior volume of the stent and detachably coupled to one or more attachment portions of the blood pump to support the blood pump within the interior volume of the stent; detaching the blood pump from the stent by unlocking the one or more arms from the one or more attachment portions of the blood pump, where once the one or more arms are release from the one or more attachment portions, the one or more arms move into radially outward in alignment with the plurality of flexible segments and out of the interior volume of the stent; and retrieving the blood pump out of the blood vessel using the retrieval sheath.

Unlocking the one or more arms may include translating the blood pump relative to the stent to release an attachment member at a distal end of each of the one or more arms that may be captured within a corresponding slotted opening of the housing of the blood pump. The attachment member may be magnetically retained the corresponding slotted opening by a magnetic material within the housing, where detaching the attachment member may include overcoming a magnetic force retaining the attachment member. The blood pump may be a blood pump or a power supply. The stent may be left within the blood vessel after the blood pump is removed from the blood vessel. The second stent may be expanded within the stent left within the blood vessel.

According to some aspects, a method of implanting a blood pump assembly into a patient's body includes: inserting into an entry blood vessel the blood pump assembly, the blood pump assembly including a blood pump having an inflow cannula and an electrical lead, the electrical lead having a first end coupled to the blood pump; advancing the blood pump assembly through the entry blood vessel and to the ascending aorta of the patient; securing the blood pump assembly within the ascending aorta such that the inflow cannula is disposed through the aortic valve and within the left ventricle; advancing a snare through a right subclavian artery or a left subclavian artery of the patient; capturing, with the snare, a second end of the electrical lead; retrieving the second end of the electrical lead through the right subclavian artery or the left subclavian artery using the snare; and attaching the second end of the electrical lead to a power supply located in a subcutaneous region of the patient's body. The power supply may be in a subclavicular region of the patient's body.

According to some aspects, a method of implanting a blood pump assembly into a patient's body includes: inserting into an entry blood vessel the blood pump assembly, the blood pump assembly including a blood pump having an inflow cannula; advancing the blood pump assembly through the entry blood vessel and to the ascending aorta of the patient; securing the blood pump assembly within the ascending aorta such that the inflow cannula is disposed through the aortic valve and within the left ventricle; advancing a first end of an electrical lead through a right subclavian artery or a left subclavian artery; and coupling the first end of the electrical lead to the blood pump, wherein a second end of the electrical lead is configured to be coupled to a power supply located in a subcutaneous region of the patient's body. The power supply may be in a subclavicular region of the patient's body.

These and other aspects are described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 19 is a flow chart of a method of implanting a blood pump assembly, according to an embodiment.

DETAILED DESCRIPTION

Figure 1:
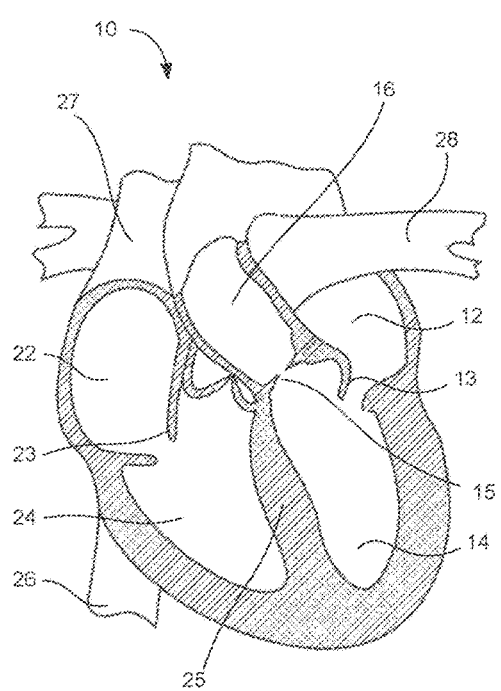
FIGS. 1 and 2 are cross-sectional schematics of the human heart.

Intracardiac pump assemblies and methods for their implantation and removal are described herein. In some embodiments, an apparatus includes an expandable member, a blood pump, and a set of struts. The expandable member, which may be a stent, is configured to transition from a collapsed configuration to an expanded configuration. The expandable member includes a set of flexible segments that form a tubular wall defining an interior volume. The flexible segments contact an inner surface of a blood vessel when the expandable member is in the expanded position. The expandable member includes a set of attachment portions. Each of the struts has a first end portion coupled to a housing of the blood pump. Each of the struts has a second end portion configured to be removably coupled to a corresponding attachment portion such that the blood pump can be removably coupled to the expandable member with at least a portion of the housing disposed within the interior volume of the expandable member.

In some embodiments, an apparatus includes an expandable member, a blood pump, a power supply, and a set of struts. The expandable member is configured to transition from a collapsed configuration to an expanded configuration. The expandable member including a set of flexible segments that form a tubular wall defining an interior volume. The flexible segments are configured to contact an inner surface of a blood vessel when the expandable member is in the expanded position. The expandable member includes a set of attachment portions. The power supply is coupled to the blood pump and is configured to provide power to drive the blood pump. Each of the struts has a first end portion coupled to at least one of the blood pump or the power supply. Each of the struts has a second end portion configured to be removably coupled to a corresponding attachment portion such that the blood pump and the power supply can be removably coupled to the expandable member with at least one of a portion of the blood pump or a portion of the power supply disposed within the interior volume of the expandable member.

In some embodiments, kit includes a blood pump assembly and a set of expandable members. The blood pump assembly includes a housing and a set of struts. Each strut has a first end portion coupled to the housing. Each of the expandable members is configured to transition from a collapsed configuration to an expanded configuration. Each of the expandable members includes a set of flexible segments that form a tubular wall defining an interior volume. The flexible segments are configured to contact an inner surface of a blood vessel when the expandable member is in the expanded position. Each of the expandable members includes a plurality of attachment portions. Each of the struts has a second end portion configured to be removably coupled to a corresponding attachment portion of each expandable member such that the blood pump can be removably coupled to each expandable member with at least a portion of the housing disposed within the interior volume of the expandable member. The set of expandable members includes a first expandable member having a first size and a second expandable member having a second size. The first size is different than the second size.

In some embodiments, a method of implanting a blood pump assembly includes inserting into an entry blood vessel the blood pump assembly. The blood pump assembly includes a blood pump, an expandable member, and a set of struts. The expandable member includes a set of flexible segments that form a tubular wall defining an interior volume. The expandable member includes a set of attachment portions. A first end portion of each strut is coupled to the blood pump. A second end portion of each strut is removably coupled to a corresponding attachment portion such that at least a portion of the blood pump is within the interior volume of the expandable member. The inserting is performed when the expandable member is in a collapsed configuration. The blood pump assembly is advanced through the entry blood vessel and to a target blood vessel. The expandable member is then transitioned from the collapsed configuration to an expanded configuration such that the flexible segments contact an inner surface of the target blood vessel and the blood pump is suspended within the target blood vessel by the struts. The blood pump and the set of struts are configured to be removed from the target blood vessel by removing the second end portion of each strut from its corresponding attachment portion.

In some embodiments, a method includes inserting into an entry blood vessel a retrieval sheath. The retrieval sheath is advanced through the entry blood vessel and to a target blood vessel. The retrieval sheath is then positioned about a proximal end portion of a blood pump from a blood pump assembly. The blood pump assembly includes the blood pump, an expandable member, and a set of struts. The expandable member includes a tubular wall in contact an inner surface of the target blood vessel and defining an interior volume. The expandable member includes a set of attachment portions. A first end portion of each strut is coupled to the blood pump, and a second end portion of each strut is coupled to a corresponding attachment portion such that at least a portion of the blood pump is within the interior volume of the expandable member and suspended within the target blood vessel. The method includes moving an end portion of the retrieval sheath distally relative to the blood pump to: A) remove the second end portion of each strut from its corresponding attachment portion, and B) place the blood pump and the set of struts within the retrieval sheath. The retrieval sheath, including the blood pump and the plurality of struts, is retracted from the target blood vessel.

In some embodiments, a method includes inserting into an entry blood vessel a blood pump assembly that includes a blood pump, an inflow cannula, and an electrical lead. The blood pump assembly is advanced through the entry blood vessel and to an ascending aorta. The blood pump assembly is then affixed within the ascending aorta such that the inflow cannula is disposed through an aortic valve and within a left ventricle. The method further includes advancing a catheter through a superior vena cava and transseptally into the left ventricle. A proximal end portion of the electrical lead is captured, and a distal end portion of the lead is configured to be coupled to the blood pump. The proximal end portion of the electrical lead is retrieved through the superior vena cava, and is attached to a power supply located in a subcutaneous region of a body.

In some embodiments, a method includes inserting into an entry blood vessel a blood pump assembly that includes a blood pump and an inflow cannula. The blood pump assembly is advanced through the entry blood vessel and to an ascending aorta. The blood pump assembly is then affixed within the ascending aorta such that the inflow cannula is disposed through an aortic valve and within a left ventricle. The method further includes advancing a distal end portion of an electrical lead through a superior vena cava and transseptally into the left ventricle. The distal end portion of the lead is coupled to the blood pump. A proximal end portion of the electrical lead is configured to be coupled to a power supply located in a subcutaneous region of a body.

The term "about" when used in connection with a referenced numeric indication means the referenced numeric indication plus or minus up to 10 percent of that referenced numeric indication. For example, "about 100" means from 90 to 110.

The term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of .+−. 10 percent of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

As used in this specification and the appended claims, the words "proximal" and "distal" refer to direction closer to and away from, respectively, an operator of the medical device or implant. Thus, for example, the end of an implant first contacting the patient's body (i.e., furthest away from the practitioner implanting the device) would be the distal end of the implant, while the end opposite the distal end would be the proximal end of the implant.

As used herein, the terms "blood vessel" or "vessel" include any structure within the body through which blood can flow to tissues and organs within the body, including any vein, artery, or capillary. For example, the term "blood vessel" can refer to a subclavian vein, a femoral artery, subclavian artery an ascending aorta, or any other structure within the human body.

Figure 2:
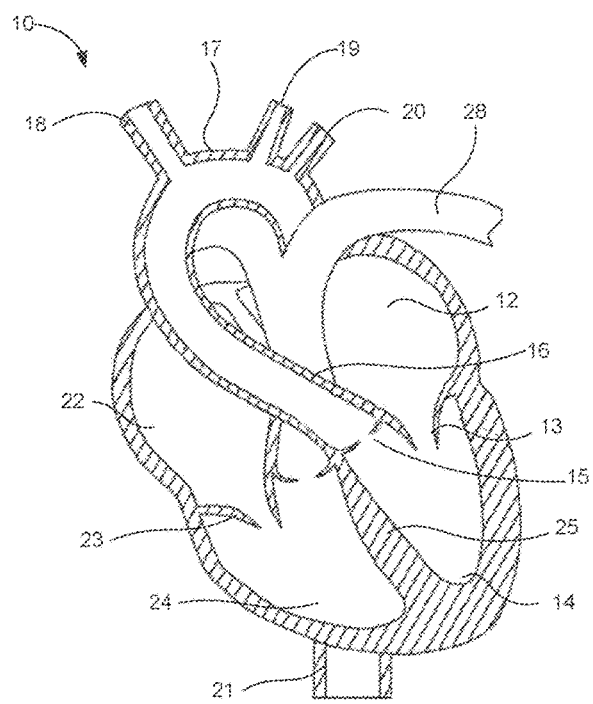

For reference, FIGS. 1 and 2 show various cross-sectional views of a human heart 10, which is an organ that pumps blood through the body via the circulatory system. The blood provides oxygen and nutrients to the tissues and removes carbon dioxide and other wastes. The heart 10 has four chambers: two upper chambers (the left atrium 12 and the right atrium 22) and two lower chambers (the left ventricle 14 and the right ventricle 24). The right atrium 22 and the right ventricle 24 together make up the right heart and the left atrium 12 and left ventricle 14 make up the left heart. A wall of muscle called the septum 25 separates the two sides of the heart.

The heart has multiple valves that separate the chambers of the heart, and control the flow of blood through the various blood vessels through which blood flows into and out of the heart 10. Specifically, the tricuspid valve 23 separates the right ventricle 22 from the right atrium 24. Blood flows from the superior vena cava 27 and the inferior vena cava 26 and into the right atrium 22. During diastole, the pressure in the ventricles drops, thus allowing the blood to flow from the right atrium 22 through the tricuspid valve 23 and into the right ventricle 24. During systole, blood flows out of the right ventricle 24 and into the pulmonary arteries (the left pulmonary artery 28 is identified in FIGS. 1 and 2).

The mitral valve 13 separates the left ventricle 12 from the left atrium 14. Oxygenated blood flows from the pulmonary veins and into the left atrium 12. During diastole, the pressure in the ventricles drops, thus allowing the blood to flow from the left atrium 12 through the mitral valve 13 and into the left ventricle 24. During systole, blood flows out of the left ventricle 14, through the aortic valve 15 and into the aorta. The aorta includes the ascending aorta 16, the aortic arch 17, and the descending aorta 21 (see FIG. 2). The aortic arch 17 supplies blood to the brachiocephalic artery 18, the left common carotid artery 19 and the left subclavian artery 20. Heartstrings (chordae tendinae) anchor the valves to the heart muscles. The sinoatrial nodes produce the electrical pulses that drive the heart contractions.

Figure 6:
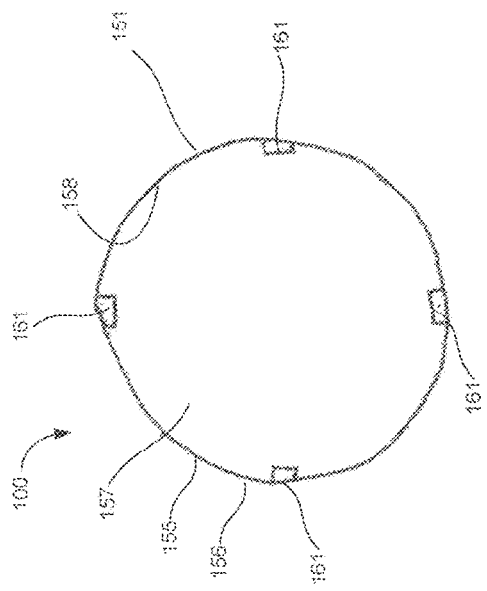

FIGS. 3-6 are schematic illustrations of a blood pump assembly 100, according to an embodiment. The blood pump assembly 100 is shown in a first configuration (FIG. 3), a second configuration (FIGS. 4 and 5) and a third configuration (FIG. 6). The blood pump assembly 100 includes a blood pump 101, a set of struts 131, and an expandable member 151. The blood pump 101 can be any suitable device that pumps blood and provides the desired flow characteristics to supplement the output of the heart. For example, the blood pump 101 (and any of the blood pumps described herein) includes a pumping unit (not shown, e.g., an impeller, a roller, a balloon, or the like) enclosed within a housing 103. The blood pump 101 produces any suitable blood flow rate, for example a flow rate of between 0.5 liters per minute and 3 liters per minute. In some embodiments, the blood pump 101 (or any of the blood pumps described herein) can produce a flow rate of between 3.0 liters per minute and 5.0 liters per minute. Moreover, the blood pump 101 (and any of the blood pumps described herein) can be configured to limit the amount of heat transfer into the blood, reduce and/or eliminate points of stasis, or the like. In some embodiments, the blood pump 101 can include a miniature axial heart pump. In some embodiments, the blood pump 101 (and any of the blood pumps described herein) can include a miniature pump similar to those developed by VADovations, Inc., and disclosed in U.S. Pat. No. 9,211,368, entitled "Heart Assist Device," which is incorporated herein by reference in its entirety. In some embodiments, the assembly 100 can include a power supply (not shown) that is close-coupled to the blood pump 101. Similarly stated, in some embodiments the assembly 100 (or any of the assemblies described herein) can include a power supply (battery, capacitance power supply, etc.) that can be disposed along with the blood pump 101 within the vasculature. In such embodiments, the assembly 100 (or any of the assemblies described herein) can also include a wireless charging system of the types shown and described herein (e.g., the wireless systems 781, 800).

The expandable member 151 is configured to transition from a collapsed configuration (FIG. 3) to an expanded configuration (FIGS. 4-6), and includes a series of flexible segments 152. The flexible segments 152 can be coupled together in any suitable pattern to form a tubular wall 155 having an outer surface 156 and an inner surface 158, and that defines an interior volume 157. The expandable member 151 can include any suitable number of flexible segments 152 in any suitable form, such as coiled members, longitudinal members, or the like. For example, in some embodiments, the flexible segments 152 can be braided or woven to produce the tubular wall 155 that can transition from the collapsed configuration to the expanded configuration. In some embodiments, the expandable member 151 can include multiple layers of flexible segments to produce the desired spring characteristics and strength. In yet other embodiments, the flexible segments 152 can be produced from a monolithic sheet of material (e.g., by a laser cutting process). Moreover, any the tubular wall 155 (and any of the tubular walls described herein) can have any suitable pore size (or arrangement of openings) so that the outer surface 156 provides the desired contact area within the bodily lumen. In this manner, as described herein, the expandable member 151 can be resistant to migration and can provide support for the blood pump 101 suspended within the interior volume 157.

The expandable member 151 and the flexible segments 152 (and any of the expandable members described herein) can be constructed from any suitable material that provides the desired strength, spring characteristics and biocompatibility. For example, in some embodiments. The expandable member 151 (and any of the expandable members described herein) can be constructed from a metal, such as, for example, a medical grade stainless steel, a cobalt-based alloy, platinum, gold, titanium, tantalum, and/or niobium. In some embodiments, the expandable member 151 (and any of the expandable members described herein) can be constructed from a shape memory material, such as a nickel-titanium alloy (e.g., Nitinol®). In other embodiments, the expandable member 151 (and any of the expandable members described herein) can be constructed from a polymeric material, such as, for example, poly(L-lactide) (PLLA), poly(D,L-lactide) (PLA), poly(glycolide) (PGA), poly(L-lactide-co-D,L-lactide) (PLLA/PLA), polyethylene terephthalate (PET), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene)poly(D,L-lactide-co-caprolactone) PLA/PCL), poly(glycolide-co-caprolactone) (PGA/PCL), poly(phosphate ester), or the like.

Figure 4:
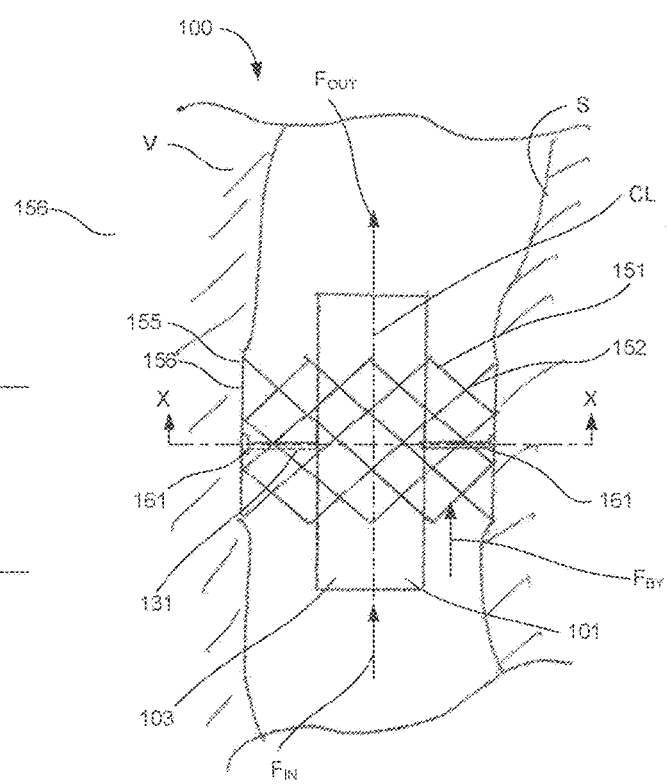
Figure 5:
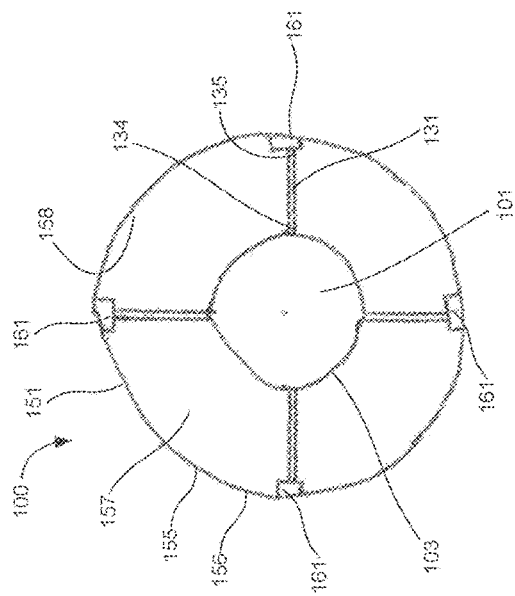
FIGS. 5 and 6 are cross-sectional views of the blood pump assembly taken along line X-X in FIG. 4 in the second configuration, and a third configuration, respectively.

As shown in FIG. 4, when the blood pump assembly 100 is deployed within a blood vessel V and the expandable member 151 is in its expanded configuration, the outer surface 156 of the tubular wall 155 is in contact with the inner surface S of the blood vessel V. The expandable member 151 is sized and configured such that the outer surface 156 exerts a radially outward force on the inner surface S to maintain (or anchor) the expandable member 151 within the blood vessel. By providing the anchoring force circumferentially and along the axial length $L_C$ of the expandable member 151 (as opposed to multiple, discrete anchor points), the expandable member 151 and the blood pump assembly 100 are resistant to migration (i.e., movement along the longitudinal center line CL) within the blood vessel V. Similarly stated, the expandable member 151 distributes the radially outward anchoring force over the contact area of the outer surface 156, thereby minimizing migration. This arrangement also minimizes and/or eliminates tipping (i.e., rotation about an axis non-parallel to the longitudinal center line CL). Moreover, by avoiding anchoring via discrete anchor points, the expandable member 151 and the blood pump assembly 100 reduces the likelihood of perforating the wall of the blood vessel V.

Figure 3:
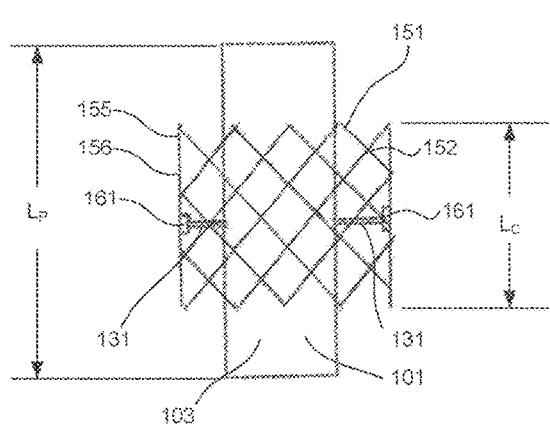
FIGS. 3 and 4 are schematic illustrations of a blood pump assembly, according to an embodiment, in a first configuration and a second configuration, respectively.

Referring to FIG. 3, the expandable member 151 has a contact length $L_C$ over which the outer surface 156 of the tubular wall 155 is in contact with the inner surface S of the blood vessel V. The contact length $L_C$ can be any suitable distance to provide the desired anchoring and/or stability characteristics. For example, in some embodiments, the contact length $L_C$ can be equal to or greater than a length $L_P$ of the blood pump 101. In other embodiments, the contact length $L_C$ can be less than a length $L_P$ of the blood pump 101. For example, in some embodiments, the contact length $L_C$ can be at least about one quarter of the length $L_P$ of the blood pump 101. In some embodiments, the contact length $L_C$ can be less than about three quarters of the length $L_P$ of the blood pump 101. In some embodiments, the contact length $L_C$ can be less than about half of the length $L_P$ of the blood pump 101. In some embodiments, the contact length $L_C$ can be less than about one quarter of the length $L_P$ of the blood pump 101.

The expandable member 151 includes a series of attachment portions 161 to which a corresponding strut 131 can be removably and/or releasably coupled. In some embodiments, the attachment portions 161 (and any of the attachment portions described herein) can be a separate structure or mechanism that is coupled to the flexible segments 152 or tubular wall 155. In other embodiments, the attachment portions 161 (and any of the attachment portions described herein) can be monolithically constructed with (or a portion of) the flexible segments 152 or tubular wall 155. Although the expandable member 151 is shown as including four attachment portions 161, in other embodiments, the expandable member 151 (and any of the expandable members described herein) can include any suitable number of attachment portions (e.g., between two and eight, between two and ten, or between two and 12). Although the attachment portions 161 are shown as extending within the internal volume 157, in other embodiments, the attachment portions 161 can be flush with the inner surface 158 of the tubular wall 155. Similarly stated, in some embodiments, the tubular wall 155 and the set of attachment portions 161 define a continuous inner surface 158.

The blood pump assembly 100 includes a set of struts 131. Each strut 131 includes a first end portion 134 and a second end portion 135. The first end portion 134 of each strut 131 is coupled to the pump 101. More particularly, the first end portion 134 of each strut 131 is coupled to the housing 103 of the pump 101. The first end portion 134 can be coupled to the housing 103 in any suitable manner. For example, in some embodiments, the first end portion 134 can be coupled by a pin joint or a ball joint, such that the strut 131 can rotate relative to the housing (e.g., when the expandable member 151 moves from its collapsed configuration to its expanded configuration). In other embodiments, the first end portion 134 can be coupled to the housing 103 by a band, weld joint, or adhesive. The second end portion 135 of each strut is removably coupled to its corresponding attachment portion 161 of the expandable member 151. In this manner, the blood pump 101 can be removably coupled to the expandable member 151 by the set of struts 131. More particularly, the blood pump 101 can be coupled to the expandable member 151 with at least a portion of the housing 103 disposed within the interior volume 157 of the expandable member 151. Similarly stated, when the blood pump assembly 100 is in its first configuration and its second configuration, the blood pump 101 is suspended within the interior volume 157 by the set of struts 131.

Because the second end portion 135 of each strut is removably (or releasably) coupled to the corresponding attachment portion 161, the blood pump 101 and the struts 131 can be removed from the expandable member 151. This arrangement allows the blood pump assembly 100 to be moved from the second configuration (FIGS. 4 and 5) to the third configuration (FIG. 6). In this manner, the blood pump 101 and the struts 131 can be removed when the assembly 100 is within the body, for example, if the patient no longer needs the pump assembly 100, if the blood pump 101 has malfunctioned, or the like. Moreover, as described in more detail below, the blood pump 101 and the struts 131 can be removed endovascularly by decoupling (or releasing) the struts 131 from the attachment portions 161.

The struts 131 can be constructed from any suitable material that provides the desired strength to suspend the blood pump 101 within the blood vessel V. Moreover, the struts 131 are flexible and can change their length and/or orientation to allow the expandable member to transition from the collapsed configuration to the expanded configuration. For example, in some embodiments, the struts 131 can be constructed from a metallic material, such as, a medical grade stainless steel. In other embodiments, the struts 131 (and any of the struts described herein) can be constructed from a shape memory material, such as a nickel-titanium alloy (e.g., Nitinol®). In other embodiments, the struts 131 (and any of the struts described herein) can be constructed from a polymeric material, such as, for example, poly(L-lactide) (PLLA), poly(D,L-lactide) (PLA), poly(glycolide) (PGA), poly(L-lactide-co-D,L-lactide) (PLLA/PLA), polyethylene terephthalate (PET), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene)poly(D,L-lactide-co-caprolactone) PLA/PCL), poly(glycolide-co-caprolactone) (PGA/PCL), poly (phosphate ester), or the like.

In some embodiments, either of the attachment portions 161 or the second end portion 135 of the struts 131 can include a latch, a locking mechanism, or detent that maintains the struts 131 within the attachment portions 161 until a retrieval force threshold has been exceeded. This arrangement prevents the struts 131 from being inadvertently released or removed from the expandable member 151.

Although the blood pump assembly 100 is shown as including four struts 131, in other embodiments, the blood pump assembly 100 (and any of the blood pump assemblies described herein) can include any suitable number of struts (e.g., between two and eight, between two and ten, or between two and 12).

In use, the blood pump assembly 100 (and any of the blood pump assemblies described herein) can be implanted into a patient's circulatory system to supplement the blood flow output of the heart. Because the blood pump 101 and the struts 131 can be removed from the expandable member 151, the blood pump assembly 100 (and any of the blood pump assemblies described herein) is well suited for both short term and long term use. For example, the blood pump assembly 100 (and any of the blood pump assemblies described herein) can be implanted, and then removed within ten days, one month, two months, or less than one year when the patient no longer needs the circulatory assistance. As described herein, the blood pump 101 and the struts 131 can be removed (leaving the expandable member 151 behind) without obstructing the blood vessel. Similarly, when implanted for long-term use (e.g., one year, two years, or longer), the blood pump 101 and the struts 131 can be removed when there is a failure of the blood pump 101, to replace the batteries (not shown) or the like.

To implant the blood pump assembly 100, the assembly 100 is first inserted into an entry blood vessel (e.g., the femoral artery) endovascularly. Similarly stated, the assembly 100 is first inserted into an entry blood vessel (e.g., the femoral artery) using percutaneous and/or minimally invasive techniques. The blood pump assembly 100 is inserted when in its first (or collapsed) configuration, as shown in FIG. 3. The blood pump assembly 100 is then advanced to a target blood vessel (identified as the blood vessel V in FIG. 4). The target blood vessel V can be any suitable blood vessel, such as the descending aorta, the aortic arch, or the ascending aorta. The blood pump assembly 100 is then transitioned from its first (or collapsed) configuration to its second (or expanded configuration). When in the expanded configuration, the outer surface 156 of the tubular wall 155 contacts, engages and/or exerts a radially outward force upon the inner surface S of the blood vessel V, as described above. In this manner, the blood pump assembly 100 can be anchored in the desired location within the blood vessel V.

After being implanted, the blood pump 101 can be actuated (or powered) to supplement the blood flow provided by the patient's heart. In particular, the blood pump 101 (and any of the blood pumps described herein) can supplement the blood flow continuously or only during diastole. As shown in FIG. 4, the blood pump 101 can receive an inlet blood flow $F_{in}$ (e.g., via an inlet cannula, not shown) and produce an outlet blood flow $F_{out}$. Because the blood pump 101 is suspended with the blood vessel V, the blood flow produced by the heart (e.g., during systole) can flow around the blood pump 101, as shown by the arrow F.sub.BY.

When removal of the blood pump 101 is desired, the struts 131 can be detached from attachment portions 161 of the expandable member 151, and the blood pump 101 and the struts 131 can be removed, as shown in FIG. 6. This can be accomplished using any tools or by any of the methods described herein. In this manner, the only structure left in the blood vessel V is the expandable member 151, which does not block the blood vessel V. By removing the struts 131 from the expandable member 151, as opposed to removing the end portion of the struts 131 directly from the inner surface S of the blood vessel, the risk of perforation or tearing of the blood vessel V is minimized Specifically, because implanted structure that is in direct contact with the inner surface S may be subject to tissue ingrowth, endothelialization, or the like, the arrangement of the assembly 100 provides a reliable way to remove the blood pump 101 via endovascular techniques and with minimal risk of damaging the blood vessel V.

Figure 7:
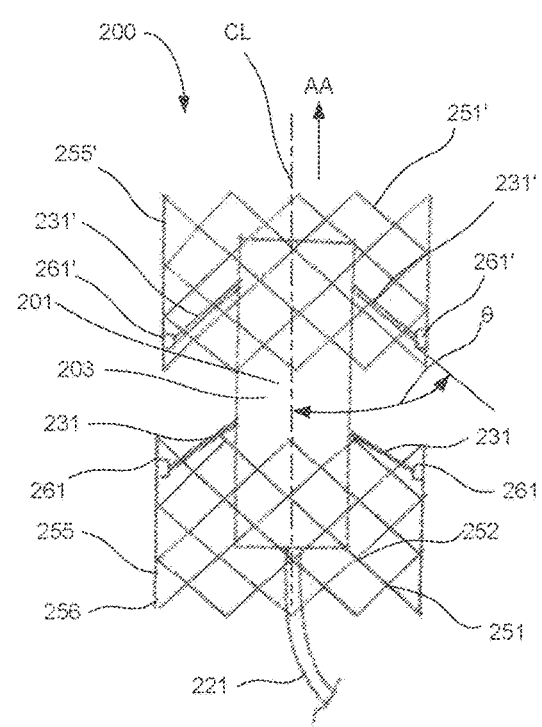
FIG. 7 is a schematic illustration of a blood pump assembly, according to an embodiment.

Although the blood pump assembly 100 is shown as including one expandable member 151, in other embodiments any of the blood pump assemblies described herein can include any number of expandable members that are removably coupled to a blood pump, a power supply or a set of struts. In this manner, the expandable assemblies can be positioned about the blood pump and/or power supply to produce the desired stability of the system (e.g., to minimize migration, tipping or the like). For example, FIG. 7 is a schematic illustration of a blood pump assembly 200, according to an embodiment. Like the blood pump assemblies 100 and 400, the blood pump assembly 200 can be transitioned between a first configuration (collapsed), a second configuration (expanded deployed) and a third configuration (pump retrieved). The blood pump assembly 200 includes a blood pump 201, two sets of struts 231, 231', and two expandable members 251, 251'. The blood pump 201 can be any suitable device that pumps blood and provides the desired flow characteristics to supplement the output of the heart. For example, the blood pump 201 (and any of the blood pumps described herein) includes a pumping unit (not shown, e.g., an impeller, a roller, a balloon, or the like)

enclosed within a housing 203. An inflow cannula 221 is coupled to the distal end portion of the housing 203, and the blood pump 201 produces an output flow in the direction indicated by the arrow AA in FIG. 7. The blood pump 201 produces any suitable blood flow rate, for example a flow rate of between 0.5 liters per minute and 3 liters per minute. In some embodiments, the blood pump 201 (or any of the blood pumps described herein) can produce a flow rate of between 1.0 liters per minute and 2.5 liters per minute. Moreover, the blood pump 201 (and any of the blood pumps described herein) can be configured to limit the amount of heat transfer into the blood, reduce and/or eliminate points of stasis, or the like.

In some embodiments, the assembly 200 can include a power supply (not shown) that is also disposed within the housing 203. In this manner, the assembly 200 (or any of the assemblies described herein) can include a power supply (battery, capacitance power supply, etc.) that can be disposed along with the blood pump 201 within the vasculature. In such embodiments, the assembly 200 (or any of the assemblies described herein) can also include a wireless charging system of the types shown and described herein (e.g., the wireless systems 781, 800).

The first expandable member 251 is coupled to the distal end portion of the housing 203, and is configured to transition from a collapsed configuration to an expanded configuration. The first expandable member 251 includes a series of flexible segments 252 coupled together in any suitable pattern to form a tubular wall 255 having an outer surface 256 and an inner surface, and that defines an interior volume. The second expandable member 251' is coupled to the proximal end portion of the housing 203, and is configured to transition from a collapsed configuration to an expanded configuration. Like the first expandable member 251, the second expandable member 251' includes a series of flexible segments coupled together in any suitable pattern to form a tubular wall 255' having an outer surface and an inner surface, and that defines an interior volume.

The expandable members 251, 251' can include any suitable number of flexible segments (e.g., the flexible segments 252) in any suitable form, such as coiled members, longitudinal members, or the like. For example, in some embodiments, the flexible segments can be braided or woven to produce the tubular wall that can transition from the collapsed configuration to the expanded configuration. In some embodiments, the expandable member can include multiple layers of flexible segments to produce the desired spring characteristics and strength. In yet other embodiments, the flexible segments can be produced from a monolithic sheet of material (e.g., by a laser cutting process). Moreover, any the tubular walls 255, 255' (and any of the tubular walls described herein) can have any suitable pore size (or arrangement of openings) so that the outer surface provides the desired contact area within the bodily lumen, as described herein. In this manner, as described herein, the expandable members 251, 251' can be resistant to migration and can provide support for the blood pump 201 (and any power supply coupled within the housing 203).

When in the expanded configuration, first expandable member 251 is spaced apart from the second expandable member 251'. In this manner, the overall length of contact between the outer surfaces of the expandable members is greater than the sum of the contact length of each of the expandable members. As shown, the overall contact length (i.e., the length along the axial centerline CL from the distal-most portion of the first expandable member 251 to the proximal-most portion of the second expandable member 251') is greater than the length of the pump 201 and/or the pump housing 203. In this manner, the "two expandable member configuration" of the assembly 200 provides the desired anchoring and/or stability characteristics. For example, in some embodiments, a ratio between the overall contact length and the length of the blood pump 201 can be at least about 1.2, 1.4, 1.6, 1.8 or 2.0. The overall length can be limited by, for example, the flexibility to advance the blood pump assembly 200 within the vasculature of the patient (e.g., through the aortic arch) using endovascular techniques, as described herein. In other embodiments, the overall contact length can be less than the length of the blood pump 201. For example, in some embodiments, a ratio between the overall contact length and the length of the blood pump 201 can be at least about 0.6, 0.8, or 0.9.

When the blood pump assembly 200 is deployed within a blood vessel (not shown) and the expandable members 251, 251' are in their expanded configurations, the outer surfaces of the tubular walls 255, 255' can contact the inner surface of the blood vessel to maintain (or anchor) the expandable members 251, 251' within the blood vessel. By providing the anchoring force circumferentially and along the axial length of each expandable member 251, 251', as well as the overall contact length, the blood pump assembly 200 is resistant to migration (i.e., movement along the longitudinal center line CL) within the blood vessel. Similarly stated, the expandable members 251, 251' distribute the radially outward anchoring force over the contact area of the outer surfaces of each expandable member, thereby minimizing migration. This arrangement also minimizes and/or eliminates tipping (i.e., rotation about an axis non-parallel to the longitudinal center line CL). Moreover, by avoiding anchoring via discrete anchor points, the expandable member 251 and the blood pump assembly 200 reduces the likelihood of perforating the wall of the blood vessel.

The first expandable member 251 and the second expandable member 251' each include a series of attachment portions 261, 261' to which a corresponding strut 231, 231' can be removably and/or releasably coupled. In some embodiments, the attachment portions 261, 261' (and any of the attachment portions described herein) can be a separate structure or mechanism that is coupled to the flexible segments or tubular wall 255, 255' of each expandable member. In other embodiments, the attachment portions 261, 261' (and any of the attachment portions described herein) can be monolithically constructed with (or a portion of) their respective flexible segments or tubular wall. Although the expandable members 251, 251' are shown as including two attachment portions 261, 261', in other embodiments, the expandable members 251, 251' (and any of the expandable members described herein) can include any suitable number of attachment portions (e.g., between two and eight, between two and ten, or between two and 12). Although the attachment portions 261, 261' are shown as extending within the internal volume, in other embodiments, the attachment portions 261, 261' can be flush with the inner surface of the tubular walls 255, 255'. Similarly stated, in some embodiments, the tubular walls 255, 255' and the respective set of attachment portions 261, 261' define a continuous inner surface.

The blood pump assembly 200 includes two sets of struts 231, 231'. The first set of struts 231 correspond to the first expandable member 251 and the second set of struts 231' correspond to the second expandable member 251'. Each strut 231, 231' includes a first end portion and a second end portion. The first end portion of each strut 231, 231' is coupled to the pump 201 and/or the housing 203. The first end portion can be coupled to the housing 203 in any suitable manner, such as a pin joint or a ball joint. In this manner, the struts 231, 231' can rotate or otherwise move relative to the housing (e.g., when the expandable members 251, 251' move from their collapsed configuration to their expanded configuration). In other embodiments, the first end portion of each strut can be coupled to the housing 203 by a band, weld joint, or adhesive. As shown, the struts 231, 231' are coupled to the housing 203 such that a longitudinal axis of the strut forms an acute strut angle .theta. with the axial centerline CL of the housing 203 (measured from the distal-most end of the axial centerline CL). Although the strut angle .theta. can change when the expandable members 251, 251' transition from their collapsed configuration to their expanded configuration, maintain the strut angle within a desired range can facilitate removal and/or collapsing of the struts during the removal process, as described herein. Although the strut angle .theta. is shown as being acute for both the first set of struts 231 and the second set of struts 231', in other embodiments, the strut angle of the first set of struts 231 can be different than the strut angle of the second set of struts 231'. For example, in some embodiments, the strut angle of the first set of struts 231 can be obtuse and the strut angle of the second set of struts 231' can be acute. In other embodiments, the strut angle of the first set of struts 231 can be acute and the strut angle of the second set of struts 231' can be obtuse. In yet other embodiments, the strut angle of the first set of struts 231 and the strut angle of the second set of struts 231' can both be obtuse.

The second end portion of each strut 231, 231' is removably coupled to its corresponding attachment portion 261, 261'. In this manner, the blood pump 201 (and/or the power supply therein) can be removably coupled to the expandable members 251, 251' by the two sets of struts 231 231'. Similarly stated, when the blood pump assembly 200 is in its first configuration and its second configuration, the blood pump 201 is suspended within the interior volume of the expandable members 251, 251' by the two sets of struts 231, 231'. Because the second end portion of each strut is removably (or releasably) coupled to the corresponding attachment portion, the blood pump 201 and the struts 231, 231' can be removed from the expandable members 251, 251' by any of the methods described herein.

In some embodiments, either of the attachment portions 261, 261' or the struts 231, 231' can include a latch, a locking mechanism, or detent that maintains the struts 231, 231' within the attachment portions 261, 261' until a retrieval force threshold has been exceeded. This arrangement prevents the struts 231, 231' from being inadvertently released or removed from the expandable member 251, 251'. Although the blood pump assembly 200 is shown as including two struts within each set of struts, in other embodiments, the blood pump assembly 200 (and any of the blood pump assemblies described herein) can include any suitable number of struts (e.g., between two and eight, between two and ten, or between two and 12).

Figure 8:
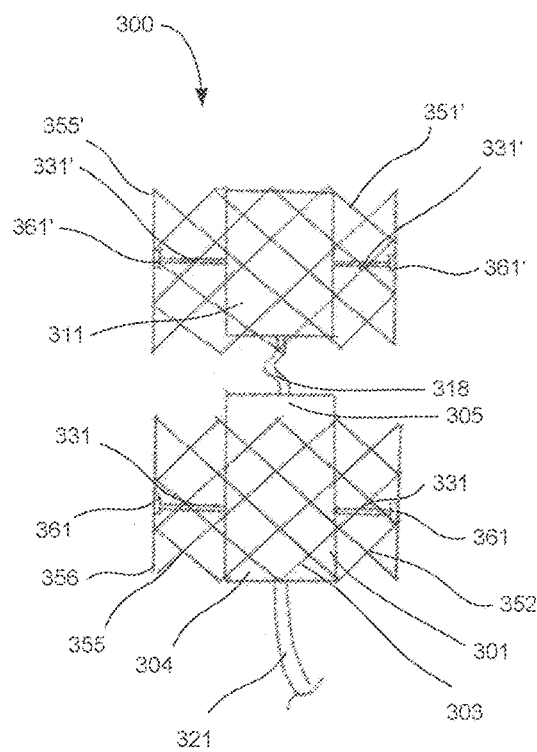
FIG. 8 is a schematic illustration of a blood pump assembly, according to an embodiment.
Figure 9:
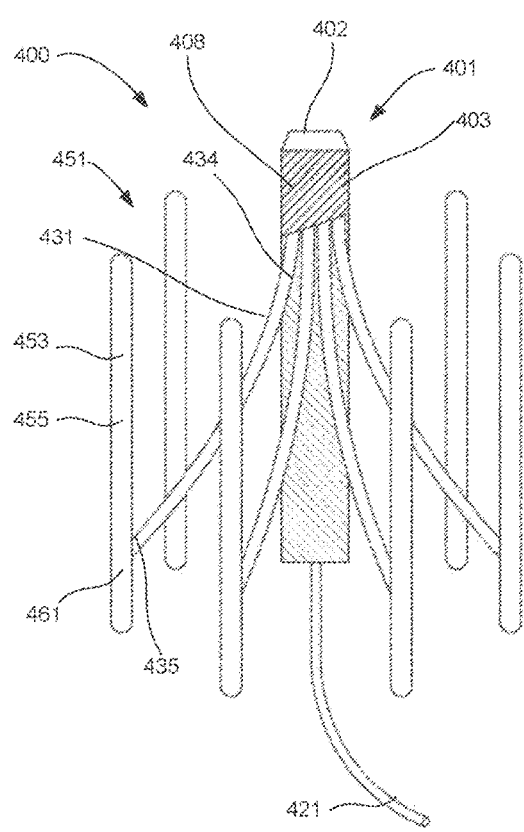
FIG. 9 is front perspective view of a blood pump assembly, according to an embodiment.

Although the housing 203 is described as including, in some embodiments, a close-coupled power supply, in other embodiments, a blood pump assembly can include a blood pump and a separately attached, but closely coupled power supply. In this manner, the power supply can be coupled along with the blood pump within the vasculature. This arrangement eliminates the need for passages, tubes, and/or wires to be extended outside of the body, and therefore this arrangement facilitates the long-term use of the pump assembly. Specifically, in some embodiments, a blood pump assembly includes a blood pump and power supply that are coupled by a flexible electrical lead that allows the pump and power supply to articulate relative to each other. In this manner, the assembly can be more easily advanced through tortuous passageways of the vasculature (e.g., the aortic arch). For example, FIG. 8 is a schematic illustration of a blood pump assembly 300, according to an embodiment. Like the blood pump assemblies 100 and 400, the blood pump assembly 200 can be transitioned between a first configuration (collapsed), a second configuration (expanded deployed) and a third configuration (pump retrieved). The blood pump assembly 300 includes a blood pump 301, a power supply 311, two sets of struts 331, 331', and two expandable members 351, 351'. The blood pump 301 can be any suitable device that pumps blood and provides the desired flow characteristics to supplement the output of the heart. For example, the blood pump 301 (and any of the blood pumps described herein) includes a pumping unit (not shown, e.g., an impeller, a roller, a balloon, or the like) enclosed within a housing 303. An inflow cannula 321 is coupled to the distal end portion 304 of the housing 303. The blood pump 301 produces any suitable blood flow rate, for example a flow rate of between 0.5 liters per minute and 3 liters per minute. In some embodiments, the blood pump 301 (or any of the blood pumps described herein) can produce a flow rate of between 1.0 liters per minute and 2.5 liters per minute. Moreover, the blood pump 301 (and any of the blood pumps described herein) can be configured to limit the amount of heat transfer into the blood, reduce and/or eliminate points of stasis, or the like.

As shown, the assembly 300 includes a power supply 311 that is coupled to the blood pump 301 by the electrical lead 318. Specifically, the electrical lead 318 is coupled to the proximal end portion 305 of the housing 303 such that the blood pump 301 and the power supply 301 are axially aligned. Moreover, the electrical lead 318 is flexible such that the pump 301 and the power supply 311 can articulate relative to each other. In this manner, the assembly 300 can be more easily advanced through tortuous passageways of the vasculature (e.g., the aortic arch). The electrical lead 318 can have any suitable length such that the power supply 311 is closely-coupled to the blood pump 301, while still maintaining the desired flexibility for implantation. For example, in some embodiments, the length of the electrical lead 318 is less than the length of the blood pump 301. Specifically, in some embodiments, the length of the electrical lead 318 can be between about 0.25 and 0.75 of the length of the blood pump 301. By maintaining a relatively short distance between the blood pump 301 and the power supply 311, the assembly 300 can be implanted in the ascending aorta without the power supply obstructing the brachiocephalic artery, the left common carotid artery, or the left subclavian artery. In other embodiments, however, the length of the electrical lead 318 can be less than the length of the blood pump 301.

The power supply 311 can include any suitable components of the types shown and described herein to provide power to the blood pump 301 within the vasculature. For example, the power supply 311 includes an energy storage member (not shown), such as a battery, a capacitance storage system, or the like. In some embodiments, the power supply 311 can also include a charging module that can be electromagnetically coupled to an external power supply (not shown). In this manner, the energy storage member (and the power supply 311) can be recharged wirelessly, allowing for long term installation of the system. The charging module can include, for example, a receiving coil (not shown) configured to be electromagnetically coupled to an external power transmission coil (not shown). The charging module can be similar to any of the charging modules or systems shown and described herein (e.g., the wireless systems 781, 800).

The first expandable member 351 is coupled to the housing 303, and is configured to transition from a collapsed configuration to an expanded configuration. The first expandable member 351 includes a series of flexible segments 352 coupled together in any suitable pattern to form a tubular wall 355 having an outer surface 356 and an inner surface, and that defines an interior volume. The second expandable member 351' is coupled to the power supply 311, and is configured to transition from a collapsed configuration to an expanded configuration. Like the first expandable member 351, the second expandable member 351' includes a series of flexible segments coupled together in any suitable pattern to form a tubular wall 355' having an outer surface and an inner surface, and that defines an interior volume.

The expandable members 351, 351' can include any suitable number of flexible segments (e.g., the flexible segments 352) in any suitable form, such as coiled members, longitudinal members, or the like. For example, in some embodiments, the flexible segments can be braided or woven to produce the tubular wall that can transition from the collapsed configuration to the expanded configuration. In some embodiments, the expandable member can include multiple layers of flexible segments to produce the desired spring characteristics and strength. In yet other embodiments, the flexible segments can be produced from a monolithic sheet of material (e.g., by a laser cutting process). Moreover, any the tubular walls 355, 355' (and any of the tubular walls described herein) can have any suitable pore size (or arrangement of openings) so that the outer surface provides the desired contact area within the bodily lumen, as described herein. In this manner, as described herein, the expandable members 351, 351' can be resistant to migration and can provide support for the blood pump 301 and the power supply 311.

When in the expanded configuration, first expandable member 351 is spaced apart from the second expandable member 351'. In this manner, the overall length of contact between the outer surfaces of the expandable members is greater than the sum of the contact length of each of the expandable members. As shown, the overall contact length (i.e., the length along the axial centerline CL from the distal-most portion of the first expandable member 351 to the proximal-most portion of the second expandable member 351') is about the same as the length of the pump 301 and the power supply 311. In other embodiments, however, a ratio between the overall contact length and the length of the collective length of the blood pump 301 and the power supply 311 can be at least about 1.2, 1.4, 1.6, 1.8 or 3.0. The overall length can be limited by, for example, the flexibility to advance the blood pump assembly 300 within the vasculature of the patient (e.g., through the aortic arch) using endovascular techniques, as described herein. In other embodiments, the overall contact length can be less than the collective length of the blood pump 301 and the power supply 311. For example, in some embodiments, a ratio between the overall contact length and the collective length of the blood pump 301 and the power supply 311 can be at least about 0.6, 0.8, or 0.9.

When the blood pump assembly 300 is deployed within a blood vessel (not shown) and the expandable members 351, 351' are in their expanded configurations, the outer surfaces of the tubular walls 355, 355' can contact the inner surface of the blood vessel to maintain (or anchor) the expandable members 351, 351' within the blood vessel. By providing the anchoring force circumferentially and along the axial length of each expandable member 351, 351', as well as the overall contact length, the blood pump assembly 300 is resistant to migration (i.e., movement along the longitudinal center line of the assembly) within the blood vessel. Similarly stated, the expandable members 351, 351' distribute the radially outward anchoring force over the contact area of the outer surfaces of each expandable member, thereby minimizing migration. This arrangement also minimizes and/or eliminates tipping (i.e., rotation about an axis non-parallel to the longitudinal center line CL). Moreover, by avoiding anchoring via discrete anchor points, the expandable member 351 and the blood pump assembly 300 reduces the likelihood of perforating the wall of the blood vessel.

The first expandable member 351 and the second expandable member 351' each include a series of attachment portions 361, 361' to which a corresponding strut 331, 331' can be removably and/or releasably coupled. In some embodiments, the attachment portions 361, 361' (and any of the attachment portions described herein) can be a separate structure or mechanism that is coupled to the flexible segments or tubular wall 355, 355' of each expandable member. In other embodiments, the attachment portions 361, 361' (and any of the attachment portions described herein) can be monolithically constructed with (or a portion of) their respective flexible segments or tubular wall. Although the expandable members 351, 351' are shown as including two attachment portions 361, 361', in other embodiments, the expandable members 351, 351' (and any of the expandable members described herein) can include any suitable number of attachment portions (e.g., between two and eight, between two and ten, or between two and 12). Although the attachment portions 361, 361' are shown as extending within the internal volume, in other embodiments, the attachment portions 361, 361' can be flush with the inner surface of the tubular walls 355, 355'. Similarly stated, in some embodiments, the tubular walls 355, 355' and the respective set of attachment portions 361, 361' define a continuous inner surface.

The blood pump assembly 300 includes two sets of struts 331, 331'. The first set of struts 331 correspond to the first expandable member 351 and the second set of struts 331' correspond to the second expandable member 351'. Each strut 331, 331' includes a first end portion and a second end portion. The first end portion of each strut 331, 331' is coupled to the pump 301 and/or the housing 303. The first end portion can be coupled to the housing 303 in any suitable manner, such as a pin joint or a ball joint. In this manner, the struts 331, 331' can rotate or otherwise move relative to the housing (e.g., when the expandable members 351, 351' move from their collapsed configuration to their expanded configuration). In other embodiments, the first end portion of each strut can be coupled to the housing 303 by a band, weld joint, or adhesive. The struts 331, 331' can be coupled to the housing 303 at any suitable strut angle .theta. with the axial centerline of the housing 303 or the power supply 311.

The second end portion of each strut 331, 331' is removably coupled to its corresponding attachment portion 361, 361'. In this manner, the blood pump 301 and the power supply 311 can be removably coupled to the expandable members 351, 351' by the two sets of struts 331 331'. Similarly stated, when the blood pump assembly 300 is in its first configuration and its second configuration, the blood pump 301 and the power supply 311 are suspended within the interior volume of the expandable members 351, 351' by the two sets of struts 331, 331'. Because the second end portion of each strut is removably (or releasably) coupled to the corresponding attachment portion, the blood pump 301, the power supply 311, and the struts 331, 331' can be removed from the expandable members 351, 351' by any of the methods described herein.

In some embodiments, either of the attachment portions 361, 361' or the struts 331, 331' can include a latch, a locking mechanism, or detent that maintains the struts 331, 331' within the attachment portions 361, 361' until a retrieval force threshold has been exceeded. This arrangement prevents the struts 331, 331' from being inadvertently released or removed from the expandable member 351, 351'. Although the blood pump assembly 300 is shown as including two struts within each set of struts, in other embodiments, the blood pump assembly 300 (and any of the blood pump assemblies described herein) can include any suitable number of struts (e.g., between two and eight, between two and ten, or between two and 12).

Figure 10:
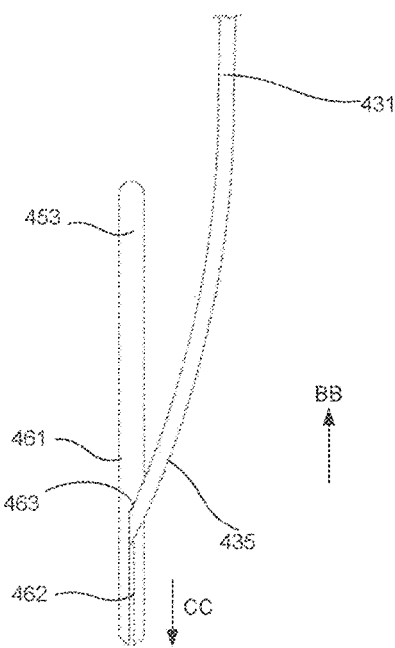
FIG. 10 is an enlarged view of a portion of the blood pump assembly shown in FIG. 9.
Figure 11:
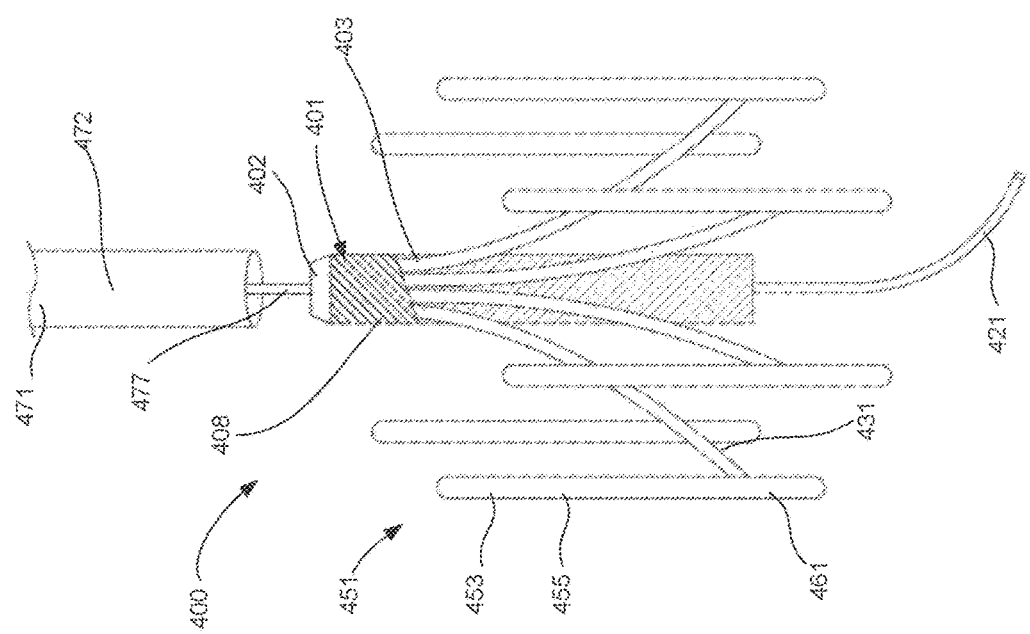
FIGS. 11-13 show the blood pump assembly shown in FIG. 9 in various stages of being transitioned from its second (or deployed) configuration and its third (or removed) configuration.
Figure 12:
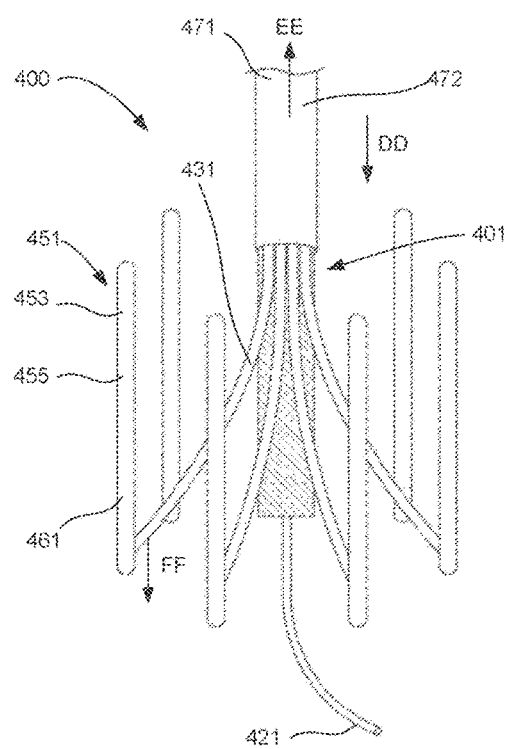
Figure 13:
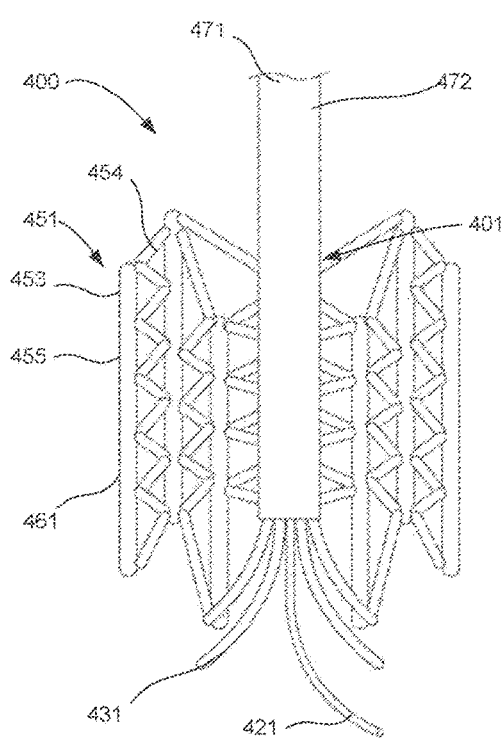

FIGS. 9-13 are show a blood pump assembly 400, according to an embodiment, that can be transitioned between a first configuration (collapsed), a second configuration (expanded and deployed) and a third configuration (pump retrieved). The blood pump assembly 400 is shown in the second configuration (FIGS. 9 and 10), and in various stages of being transitioned to the third configuration (FIGS. 11-13). The blood pump assembly 400 includes a blood pump 401, a set of struts 431 (only one strut is labeled), and an expandable member 451. The blood pump 401 can be any suitable device that pumps blood and provides the desired flow characteristics to supplement the output of the heart. For example, the blood pump 401 (and any of the blood pumps described herein) includes a pumping unit (not shown, e.g., an impeller, a roller, a balloon, or the like) enclosed within a housing 403. The blood pump 401 produces any suitable blood flow rate, for example a flow rate of between 0.5 liters per minute and 3 liters per minute. In some embodiments, the blood pump 401 (or any of the blood pumps described herein) can produce a flow rate of between 1.0 liters per minute and 2.5 liters per minute. In some embodiments, the assembly 400 can include a power supply (not shown) that is close-coupled to the blood pump 401, either within the housing 403 or within a separate housing (e.g., similar to the power supply 311 described above). Similarly stated, in some embodiments the assembly 400 (or any of the assemblies described herein) can include a power supply (battery, capacitance power supply, etc.) that can be disposed along with the blood pump 401 within the vasculature. In such embodiments, the assembly 400 (or any of the assemblies described herein) can also include a wireless charging system of the types shown and described herein (e.g., the wireless systems 781, 800).

The proximal end of housing 403 includes a proximal attachment portion 402 and an attachment band 408. The proximal attachment portion 402 is used for retrieval of the pump, as described herein, and can include any mechanism for attaching the retrieval wire 477 to the pump 401 (see FIG. 11). For example, in some embodiments, the proximal attachment portion 402 can include a hook, a threaded portion, a magnetic coupling mechanism, or the like. The distal end portion of the housing 403 is coupled to an inflow cannula 421.

The expandable member 451 is configured to transition from a collapsed configuration (not shown) to an expanded configuration (FIGS. 9-13), and includes a series of flexible segments. The flexible segments include both longitudinal segments 453 and lateral segments 454 (see FIG. 13), which can be coupled together in any suitable pattern to form a tubular wall 455. The tubular wall 455 has an outer surface and an inner surface, and defines an interior volume, similar to that formed by the expandable members 151, 251, 351 described herein. The expandable member 451 can include any suitable number of flexible segments in any suitable form, such as coiled members, longitudinal members, or the like. For example, in some embodiments, the flexible segments (e.g., the lateral segments 454) can be braided or woven to produce the tubular wall 455 that can transition from the collapsed configuration to the expanded configuration. In some embodiments, the expandable member 451 can include multiple layers of flexible segments to produce the desired spring characteristics and strength. In yet other embodiments, the flexible segments can be produced from a monolithic sheet of material (e.g., by a laser cutting process). Moreover, any the tubular wall 455 (and any of the tubular walls described herein) can have any suitable pore size (or arrangement of openings) so that the outer surface provides the desired contact area within the bodily lumen. In this manner, the expandable member can be resistant to migration and can provide support for the blood pump 401 suspended within the interior volume.

When the blood pump assembly 400 is deployed within a blood vessel (not shown) and the expandable member 451 is in its expanded configuration, the outer surface of the tubular wall 455 is in contact with an inner surface of the blood vessel. The expandable member 451 is sized and configured such that the outer surface exerts a radially outward force on the inner surface to maintain (or anchor) the expandable member 451 within the blood vessel. By providing the anchoring force circumferentially and along the axial length of the expandable member 451 (as opposed to multiple, discrete anchor points), the expandable member 451 and the blood pump assembly 400 are resistant to migration (i.e., movement along the longitudinal center line) within the blood vessel. This arrangement also minimizes and/or eliminates tipping (i.e., rotation about an axis non-parallel to the longitudinal center line). Moreover, by avoiding anchoring via discrete anchor points, the expandable member 451 and the blood pump assembly 400 reduces the likelihood of perforating the wall of the blood vessel.

The expandable member 451 includes a series of attachment portions 461 (only one is labeled) to which a corresponding strut 431 can be removably and/or releasably coupled. Although the attachment portions 461 are shown as being monolithically constructed along with the longitudinal segments 453, in other embodiments, the attachment portions 461 (and any of the attachment portions described herein) can be a separate structure or mechanism that is coupled to the longitudinal segments 453 or tubular wall 455. Moreover, because the attachment portions 461 are monolithically constructed as a part of the longitudinal segments 453, the attachment portions 461 do not extend into or otherwise obstruct the interior volume of the expandable member. Similarly stated, the attachment portions 461 can be flush with (or form a continuous surface with) the inner surface 458 of the tubular wall 455. In this manner, when the blood pump 401 is removed and the expandable member 451 is left within the body, the blood vessel will remain unobstructed. This arrangement also facilitates the implantation of a second blood pump assembly at the same location as (or on top of) the remaining expandable member. Although the expandable member 451 is shown as including six attachment portions 461, in other embodiments, the expandable member 451 (and any of the expandable members described herein) can include any suitable number of attachment portions (e.g., between two and eight, between two and ten, or between two and 12).

Referring to FIG. 10, each attachment portion 461 defines a slot 462 within which the second end portion 435 of the corresponding strut 431 can be slidingly disposed. Moreover, each attachment portion 461 includes a shoulder 463 or "end stop" that resists movement of the second end portion 435 of the corresponding strut 431. In this manner, when the assembly 400 is in the second (deployed) configuration, the second end portion 435 of each strut 431 is disposed within its corresponding slot 462, and is in contact with the shoulder 463. This arrangement prevents movement of the struts 431 in the direction indicated by the arrow BB in FIG. 10. The direction BB is also the direction of blood flow, and thus, the force exerted by the flow of blood produced by the heart acts to maintain the second end portion 435 in contact with the shoulder 463. Thus, when the assembly 400 is in the second (deployed) configuration, the second end portion 435 of each strut 431 is firmly and stably attached to the corresponding attachment portion 461.

As described in more detail below, to remove the blood pump 401 and the struts 431, a distal force (as indicated by the arrow CC) is applied to the struts 431. When the distal retrieval force exceeds a threshold value, the second end portion 435 of the corresponding strut 431 can slide distally within the slot 462 to a position outside (and released from) the attachment portion 461. In some embodiments, either of the attachment portions 461 or the second end portion 435 of the struts 431 can include a latch, a locking mechanism, or detent that maintains the struts 431 within their respective slots 462 until the retrieval force threshold has been exceeded. This arrangement prevents the struts 431 from being inadvertently released or removed from the expandable member 451.

The blood pump assembly 400 includes a set of struts 431. Each strut 431 includes a first end portion 434 and a second end portion 435. The first end portion 434 of each strut 431 is coupled to the housing 403 by the attachment band 408. In other embodiments, however, the first end portion 434 can be coupled by a pin joint or a ball joint, such that the strut 431 can rotate relative to the housing (e.g., when the expandable member 451 moves from its collapsed configuration to its expanded configuration). In other embodiments, the first end portion 434 can be coupled to the housing 403 by weld joint or adhesive.

As described above, the second end portion 435 of each strut is removably coupled within the slot 462 of its corresponding attachment portion 461 of the expandable member 451. In this manner, the blood pump 401 can be removably coupled to the expandable member 451 by the set of struts 431. More particularly, the blood pump 401 can be coupled to the expandable member 451 with at least a portion of the housing 403 disposed within the interior volume (not identified) of the expandable member 451. In some embodiments, the second end portion 435 can include a hook, latch, or the like that engages the shoulder 463. Similarly stated, in some embodiments, the second end portion 435 includes a protrusion having a longitudinal centerline that is offset from a centerline of the strut 431 (i.e., a curved or hooked portion). In some embodiments, the second end portion 435 of the struts 431 can include a latch, a locking mechanism, or detent that maintains the struts 431 within the slot 462 until a retrieval force threshold has been exceeded.

Because the second end portion 435 of each strut is removably (or releasably) coupled to the corresponding attachment portion 461, the blood pump 401 and the struts 431 can be removed from the expandable member 451. This arrangement allows the blood pump assembly 400 to be moved from the second configuration (FIGS. 9 and 10) to the third configuration (FIG. 13). In this manner, the blood pump 401 and the struts 431 can be removed when the assembly 400 is within the body, for example, if the patient no longer needs the pump assembly 400, if the blood pump 401 has malfunctioned, or the like. Moreover, the blood pump 401 and the struts 431 can be removed endoscopically by decoupling (or releasing) the struts 431 from the attachment portions 461.

Although the blood pump assembly 400 is shown as including four struts 431, in other embodiments, the blood pump assembly 400 (and any of the blood pump assemblies described herein) can include any suitable number of struts (e.g., between two and eight, between two and ten, or between two and 12).

In use, the blood pump assembly 400 (and any of the blood pump assemblies described herein) can be implanted into a patient's circulatory system to supplement the blood flow output of the heart. Any suitable endovascular, minimally-invasive and/or percutaneous techniques can be used to implant the blood pump assembly 400, according to any of the methods described herein. Moreover, because the blood pump 401 and the struts 431 can be removed from the expandable member 451, the blood pump assembly 400 (and any of the blood pump assemblies described herein) is well suited for both short term and long term use. For example, the blood pump assembly 400 (and any of the blood pump assemblies described herein) can be implanted, and then removed within ten days, one month, two months, or less than one year when the patient no longer needs the circulatory assistance. As described herein, the blood pump 401 and the struts 431 can be removed (leaving the expandable member 451 behind) without obstructing the blood vessel. Similarly, when implanted for long-term use (e.g., one year, two years, or longer), the blood pump 401 and the struts 431 can be removed when there is a failure of the blood pump 401, to replace the batteries (not shown) or the like.

To implant the blood pump assembly 400, the assembly 400 is first inserted into an entry blood vessel (e.g., the femoral artery) endovascularly. Similarly stated, the assembly 400 is first inserted into an entry blood vessel (e.g., the femoral artery) using percutaneous and/or minimally invasive techniques. The blood pump assembly 400 is inserted when in its first (or collapsed) configuration. The blood pump assembly 400 is then advanced to a target blood vessel (not shown). The target blood vessel can be any suitable blood vessel, such as the descending aorta, the aortic arch, or the ascending aorta. The blood pump assembly 400 is then transitioned from its first (or collapsed) configuration to its second (or expanded configuration). When in the expanded configuration, the outer surface of the tubular wall 455 contacts, engages and/or exerts a radially outward force upon the inner surface of the blood vessel to anchor the blood pump assembly 400 within the blood vessel.

After being implanted, the blood pump 401 can be actuated (or powered) to supplement the blood flow provided by the patient's heart. In particular, the blood pump 401 (and any of the blood pumps described herein) can supplement the blood flow continuously or only during diastole. As shown in FIG. 4, the blood pump 401 can receive an inlet blood flow via the inlet cannula 421 and produce an outlet blood flow. Because the blood pump 401 is suspended with the blood vessel, the blood flow produced by the heart (e.g., during systole) can flow around the blood pump 401.

When removal of the blood pump 401 is desired, the struts 431 can be detached from attachment portions 461 of the expandable member 451, and the blood pump 401 and the struts 431 can be removed. Referring to FIG. 11, a retrieval tool 471 is advanced to the target blood vessel using endovascular techniques as described herein. The retrieval tool 471 includes a retrieval wire 477 and a retrieval sheath 472. The retrieval wire is coupled to the proximal attachment portion 402. As shown by the arrow EE in FIG. 12, a proximal force can be exerted on the pump housing 403 to maintain the pump 401 within the blood vessel at a desired and/or constant position. The retrieval sheath 472 is advanced distally as shown by the arrow DD. An edge of the retrieval sheath 472 contacts the struts 431 as the sheath moves distally, thereby exerting a distal force upon the struts 431. When the distal force is sufficient to overcome the retrieval force threshold (e.g., the resistance of the blood flow, the resistance of the detent, etc.), each of the struts 431 moves distally within the slots 462, as shown by the arrow FF in FIG. 12. Continued movement of the sheath 472 releases the struts 431 from their respective attachment portions 461, and allows the blood pump 461 and the struts 431 to be enclosed within the sheath 472 for withdrawal from the body.

Removal in this manner leaves only the expandable member 451 with the blood vessel, which does not block the blood vessel. The design of the expandable member 451 can facilitate installation of a second (e.g., a replacement) pump assembly directly on top of the existing expandable member. Moreover, by removing the struts 431 from the expandable member 451, as opposed to removing the end portion of the struts 431 directly from the inner surface of the blood vessel, the risk of perforation or tearing of the blood vessel is minimized Specifically, because implanted structure that is in direct contact with the inner surface may be subject to tissue ingrowth, endothelialization, or the like, the arrangement of the assembly 400 provides a reliable way to remove the blood pump 401 via endovascular techniques and with minimal risk of damaging the blood vessel.

Figure 14:
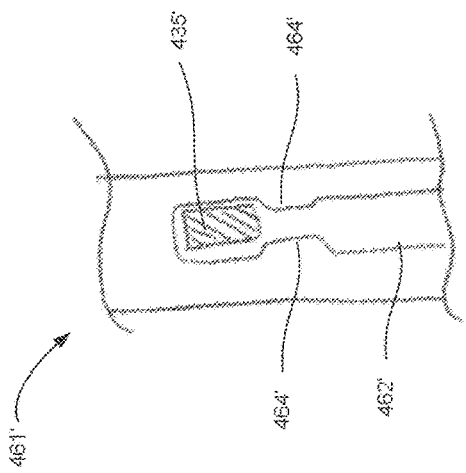
FIGS. 14 and 15 are schematic illustrations of attachment portions according to various embodiments.

Although the attachment portions 461 are shown and described above as defining the slots 462 within which the second end portion 435 of the respective strut 431 is disposed, in other embodiments, the struts can define the slots within which a protrusion of the attachment portions are slidingly disposed. Moreover, any suitable detent or resistance mechanism can be included. For example, FIG. 14 shows an attachment portion 461' that defines a slot 462' within which a strut 435' can be disposed. The attachment portion 461' includes protrusions 464' that resist the distal movement of the strut 435' until a retrieval force threshold has been exceed.

Figure 15:
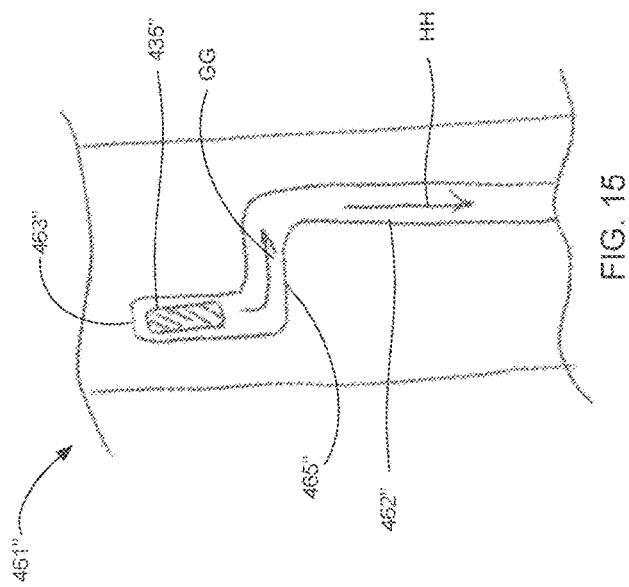

FIG. 15 shows an attachment portion configured to enable a "twist-lock" type retrieval mechanism. In particular, FIG. 15 shows an attachment portion 461" that defines a slot 462" within which a strut 435" can be disposed. The slot 462" is bounded by a proximal shoulder 463" that prevents proximal movement of the strut 435" and a twist-lock shoulder 465" that limits (but does not prevent) distal movement of the strut 435" during retrieval. To remove the strut 435" the strut 435" must be rotated as indicated by the arrow GG before it can be moved distally within the slot (arrow HH).

Figure 16:
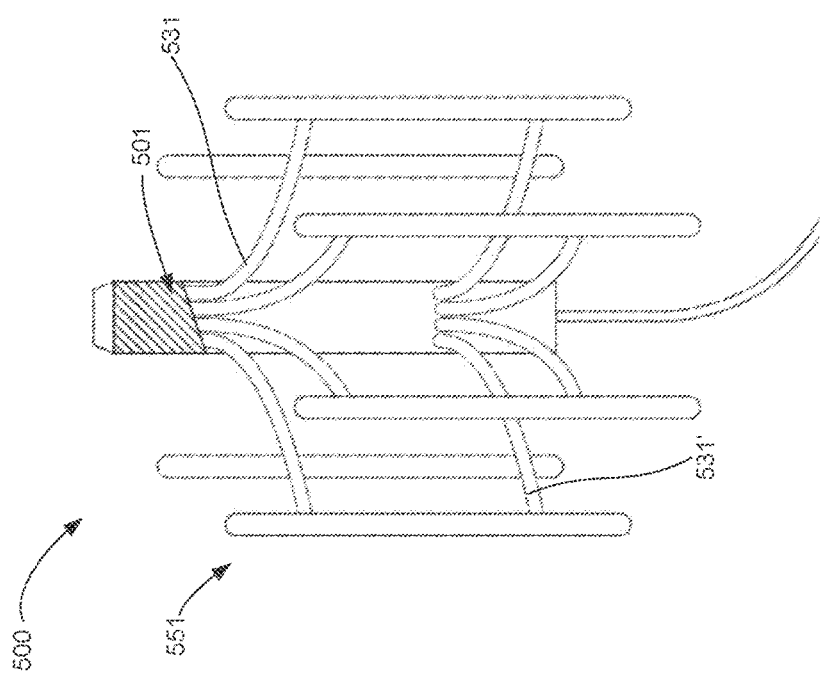
FIG. 16 is front perspective view of a blood pump assembly, according to an embodiment.

Although the blood pump assembly 400 is shown as including one set of struts 431 that is coupled to the proximal end portion of the housing 403, in other embodiments, a blood pump assembly can include any number of struts that are coupled to the pump and/or the power supply in any suitable axial locations. For example, in some embodiments, a blood pump assembly can include multiple sets of struts that couple to the housing, the blood pump and/or the power supply at multiple different axial locations. In this manner, the assembly can reduce the likelihood of tipping and increase the stability of the blood pump within the vasculature. For example, FIG. 16 shows a blood pump assembly 500, according to an embodiment, that can be transitioned between a first configuration (collapsed), a second configuration (expanded and deployed) and a third configuration (pump retrieved). The blood pump assembly 500 includes a blood pump 501, a first set of struts 531 (only one strut is labeled), a second set of struts 531' (only one strut is labeled), and an expandable member 551. The blood pump 501 is similar to the blood pump 401 (and any other blood pump described herein), and is therefore not described in detail. The expandable member 551 is similar to the expandable member 451 in many respects, and is not described in detail. The expandable member 551 differs from the expandable member 451, however, in that the expandable member 551 includes multiple sets of attachment portions (not identified), each corresponding to a strut within the different sets of struts 531, 531'. The attachment portions can be similar to the attachment portions 461 described above. The first set of struts 531 is coupled to the proximal end portion of the blood pump 501, and the second set of struts 531' is coupled to the central portion of the blood pump 501. In this manner, the two sets of struts 531, 531' provide resistance against tipping.

Figure 17:
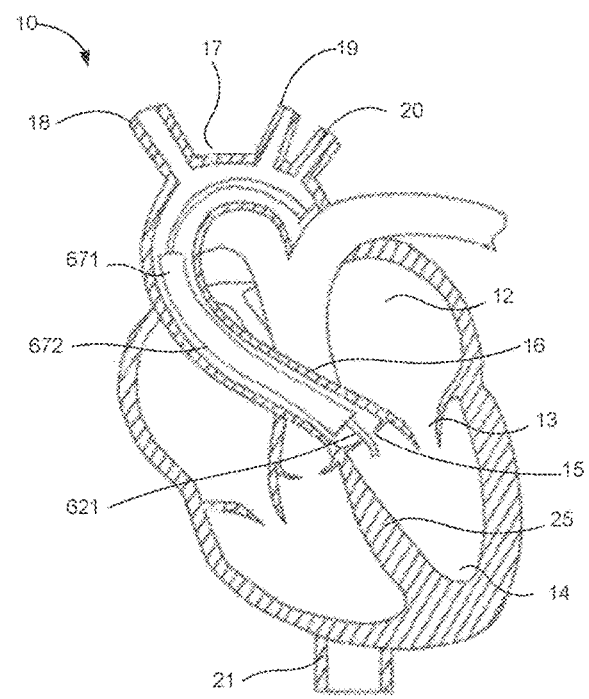
FIGS. 17 and 18 are schematic illustrations showing a method of implanting a blood pump assembly, according to an embodiment.
Figure 18:
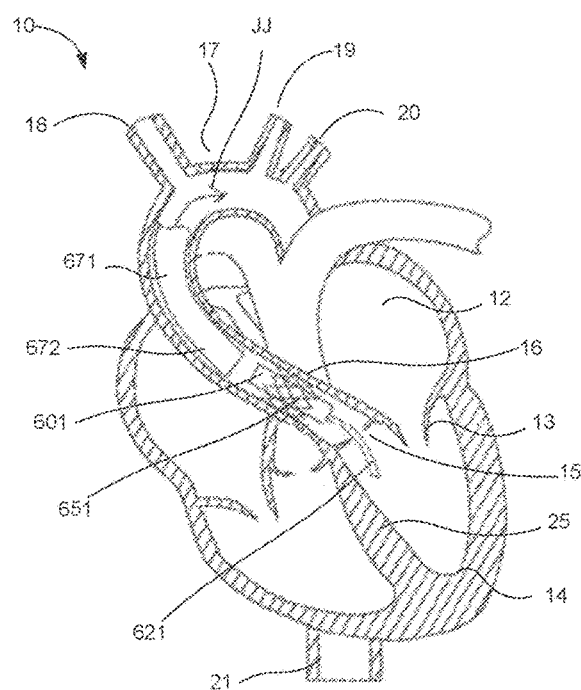

In some embodiments, any of the blood pump assemblies shown and described herein can be implanted to any suitable target blood vessel endovascularly. FIG. 19 is a flow chart of a method 40 of implantation of a blood pump assembly, according to an embodiment. The method 40 is also illustrated in FIGS. 17 and 18, which show a schematic illustration of the method of implantation with the heart 10. The method 40 can performed using any of the blood pump assemblies described herein. Although the schematic illustrations in FIGS. 17 and 18 show a blood pump 601 (having an inflow cannula 621) and an expandable member 651, the method can be performed using any of the blood pump assemblies described herein.

The method 40 includes inserting into an entry blood vessel a blood pump assembly, at 42. The blood pump assembly includes a blood pump (see e.g., blood pump 601), an expandable member (see e.g., expandable member 651), and a set of struts (not shown in FIG. 18). The expandable member includes a set of flexible segments that form a tubular wall defining an interior volume, similar to any of the expandable members described herein. The expandable member includes a set of attachment portions. A first end portion of each strut is coupled to the blood pump, and a second end portion of each strut is removably coupled to a corresponding attachment portion such that at least a portion of the blood pump is within the interior volume of the expandable member. As shown in FIG. 17, the inserting performed when the expandable member is in a collapsed configuration.

In some embodiments, the inserting optionally includes percutaneously inserting a catheter (see e.g., the catheter assembly 671 including the sheath 672) that contains the blood pump assembly into the entry blood vessel. In some embodiments, the method includes inserting the blood pump assembly percutaneously into a femoral artery.

Although FIGS. 17 and 18 show the implantation of a blood pump 601, in some embodiments, the method 40 includes inserting a blood pump assembly that includes a power supply coupled to the blood pump and configured to provide power to drive the blood pump. For example, in some embodiments, the method includes inserting a blood pump assembly that includes an integrated power supply (e.g., the assembly 200). In other embodiments, the method includes inserting a blood pump assembly that includes a close-coupled power supply (e.g., the assembly 300).

The blood pump assembly is then advanced through the entry blood vessel and to a target blood vessel, at 44. As shown by the arrow II in FIG. 17, in some embodiments, the catheter assembly 671 can be advanced in a retrograde manner within the descending aorta, through the aortic arch and into the ascending aorta. Thus, in some embodiments, the target blood vessel is the ascending aorta, and the advancing can be performed until the inflow cannula (see cannula 621 in FIGS. 17 and 18) is advanced through the aortic valve and into the left ventricle.

The expandable member is then transitioned from the collapsed configuration to an expanded configuration such that the flexible segments contact an inner surface of the target blood vessel (e.g., the ascending aorta), at 46. In this manner, the blood pump is suspended within the target blood vessel by the struts. The transitioning can be performed by any suitable method. For example, in some embodiments, the sheath 672 can be moved proximally, as shown by the arrow JJ in FIG. 18 to allow the expandable member to be moved outside of the sheath. In some embodiments, the tubular wall of the expandable member is constructed from a shape memory material such that the expandable member assumes its expanded configuration after being removed from the sheath 672. In other embodiments, the catheter assembly 671 can include a balloon that is disposed at least partially within the interior volume of the expandable member. In such embodiments, the balloon can be inflated to exert a radially outward force on the tubular wall to urge the transition from the collapsed configuration to the expanded configuration.

As described herein, the blood pump and the struts are configured to be removed from the target blood vessel by removing the second end portion of each strut from the corresponding attachment portion. Thus, in some embodiments, the method 40 optionally includes removing the second end portion of each strut from the corresponding attachment portion from the plurality of attachment portions when the expandable member is in its expanded configuration within the target blood vessel, at 48. The struts can be removed by any of the methods (or mechanisms) shown and described herein. For example, in some embodiments, the struts can be similar to the struts 431 and can be removed by the methods shown and described above with reference to the blood pump assembly 400. In some embodiments, the method 40 optionally retrieving the blood pump and the plurality of struts from the target blood vessel, at 49.

Figure 20:
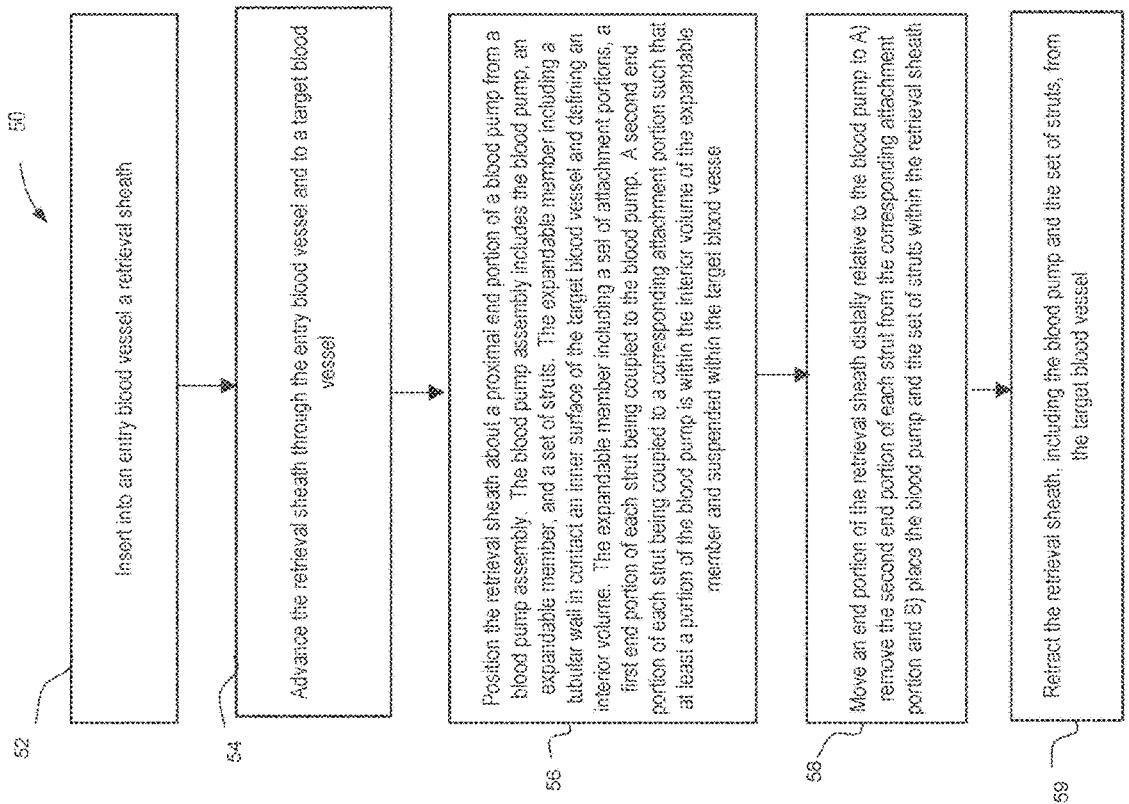
FIG. 20 is a flow chart of a method of retrieving a blood pump assembly, according to an embodiment.

In some embodiments, any of the blood pump assemblies shown and described herein can be retrieved from any of the target blood vessels endovascularly. FIG. 20 is a flow chart of a method 50 of retrieving a blood pump assembly, according to an embodiment. The method 50 can performed using any of the blood pump assemblies described herein. For example, in some embodiments, the method of retrieval can be performed on the blood pump assembly 400 (and using the retrieval tool 471) shown and described in FIGS. 9-13.

The method 50 includes inserting into an entry blood vessel a retrieval sheath, at 52. The entry blood vessel can be, for example, a femoral artery. In other embodiments, however, the entry blood vessel can be any suitable vessel. Moreover, in some embodiments, the inserting can be performed percutaneously.

The retrieval sheath is then advanced through the entry blood vessel and to a target blood vessel, at 54. The target blood vessel can be, for example, the ascending aorta. In other embodiments, however, the target blood vessel can be the descending aorta or any other vessel within the body.

The retrieval sheath is positioned about a proximal end portion of a blood pump from a blood pump assembly, at 56. Referring to FIGS. 9-13, the blood pump assembly includes the blood pump, an expandable member, and a set of struts. The expandable member including a tubular wall in contact an inner surface of the target blood vessel and defining an interior volume. The expandable member includes a set of attachment portions. A first end portion of each strut is coupled to the blood pump, and a second end portion of each strut is coupled to a corresponding attachment portion such that at least a portion of the blood pump is within the interior volume of the expandable member and suspended within the target blood vessel.

An end portion of the retrieval sheath is moved distally relative to the blood pump. At 58. This operation is performed to A) remove the second end portion of each strut from the corresponding attachment portion and B) place the blood pump and the plurality of struts within the retrieval sheath. In some embodiments, movement of the end portion of the retrieval sheath distally relative to the blood pump causes removal of the second end portion of each strut from within a slot defined by the corresponding attachment portion. In some embodiments, movement of the end portion of the retrieval sheath distally relative to the blood pump includes rotating the blood pump and struts relative to the expandable member to "unlock" the struts from the corresponding attachment portion. In some embodiments, movement of the end portion of the retrieval sheath distally relative to the blood pump is accompanied by application of a proximal force to the blood pump to maintain the blood pump relative to the expandable member.

The retrieval sheath, including the blood pump and the plurality of struts, is then retracted from the target blood vessel, at 59.

As described above, in some embodiments, any of the blood pump assemblies can include a self-contained and/or close coupled power supply. In this manner, the assembly can include a power supply (battery, capacitance power supply, etc.) that can be disposed along with the blood pump within the vasculature. The power supply (e.g., the power supply 311) can include any suitable battery of different sizes, made from different material or cell packs. The battery can also be configured to be charged or discharged at slow or fast rate. In some embodiments, the internal power supply includes a re-chargeable battery or an ultra-capacitor. The power supply powers the electronics involved, pump, and other control circuitry for programming of the pump.

In some embodiments, any of the power supplies described herein can include and/or be coupled to a control system at the implant site or outside can perform power management and adjust for sleep mode, idle mode, activation and improved operational mode based on the history of use of the assembly.

Figure 21:
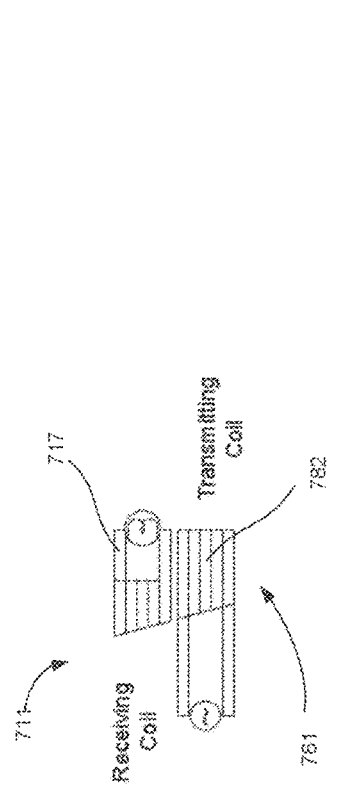
FIGS. 21-23 are schematic illustrations of inductance and resonance technology that can be used with any of the systems described herein, according to an embodiment.
Figure 22:
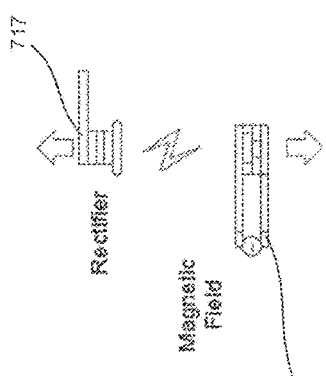
Figure 23:
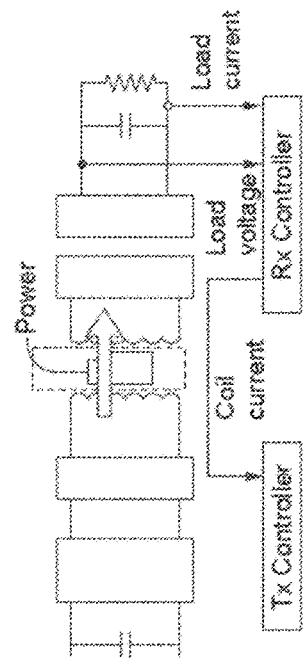

In some embodiments, any of the assemblies described herein can also include an external power source, control system and/or wireless charging system. For example, the external power source (not shown) can be situated in proximity of the subject with implanted blood pump assembly containing the internal power supply. The external power source can be portable and can be placed near the patient within which the blood pump assembly is implanted. In some embodiments, any of the systems described herein can include a wireless power transmission system. The wireless power transmission system may be implemented using any suitable system architecture and resonator design. In some embodiments, the external power supply can charge the internal power supply wirelessly and by means of magnetic resonance as well. For example, FIGS. 21-23 are schematic illustrations of applicable inductance and resonance technology that can be used with any of the systems described herein. Specifically, these figures show a portion of an internal power supply 711 and an external power/charging system 781. Collectively, these systems include a pair of coils that include a receiving coil 717 and a transmitting coil 782. The electromagnetic induction method operates based on the electromagnetic force that arises between coils in the presence of a magnetic flux. As shown in FIG. 22, the magnetic field passes between the receiving coil 717 and the transmitting coil 782. As will be appreciated by those skilled in the art, the receiving coil and transmitting coil can be off axis, as shown. As shown in FIG. 23, power passes from the transmitting coil 782 to the receiving coil 717. In some embodiments, the internal power supply can include a rectifier with a DC converter.

Figure 24:
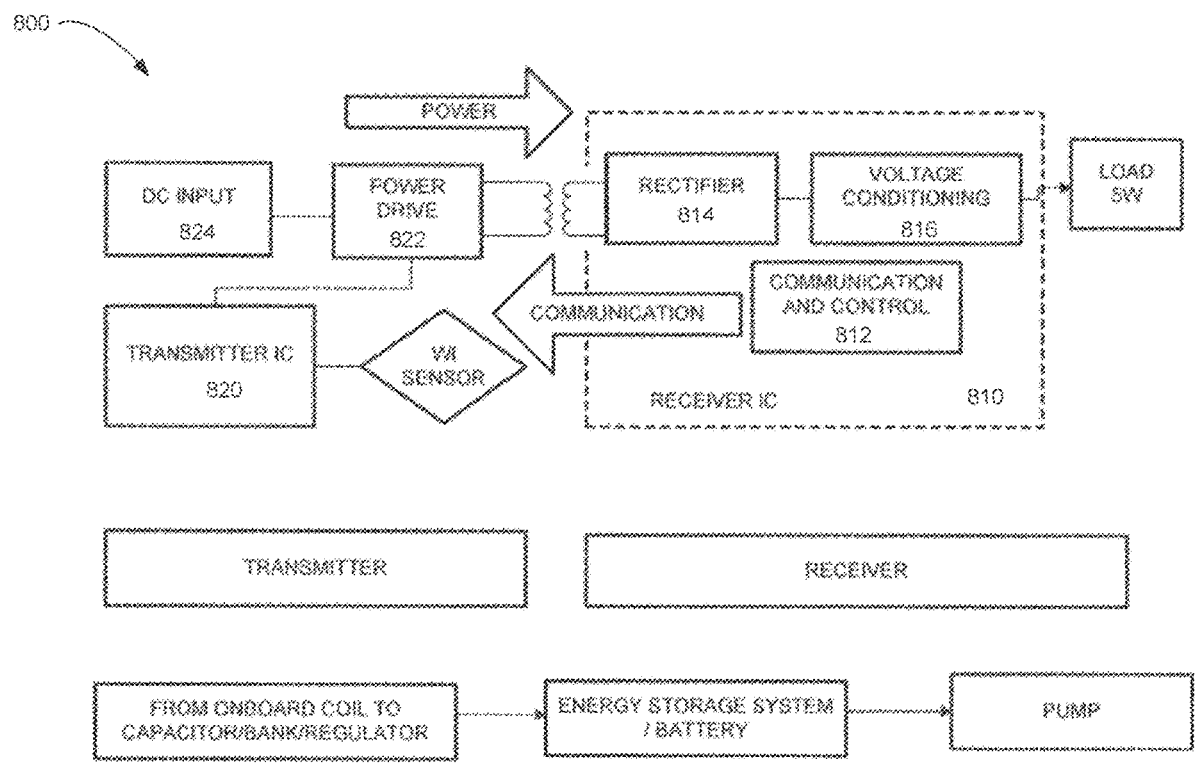
FIG. 24 is a block diagram of a wireless charging system, according to an embodiment, that can be used to power any of the blood pump assemblies described herein.

FIG. 24 is a block diagram of a wireless charging system 800 suitable to power any of the blood pump assemblies described herein. A rectifier IC 810 has a communication module and a controller 812 in communication with a rectifier 814 and a voltage conditioner 816. The rectifier IC 810 is in communication with a transmitter IC 820 that has a power drive 822 and a DC input 824. Power is transmitted from the transmitter IC 820 to the rectifier IC 810. The system can be equipped with a charging system that employs magnetic resonance (resonant inductive coupling). The near field method transmits power wirelessly over a space utilizing resonance phenomena and the transmitter coil and receiver coil oscillates (or resonates) at the same frequency which is determine by the material and shape of the coil. In one configuration, the system uses magnetic induction and n another configuration magnetic resonance.

As will be appreciated by those skilled in the art, the system can operate under relevant standards, e.g. Alliance for Wireless Power (A4WP) for implementation in MI (Q!, WPC, etc.). Energy from the on-board coil is transferred to a capacitor, for example, which is transferred to an energy storage system such as a battery, and then to the implanted vascular pump. The configuration of the system allows for wireless charging. The system described capable of charging multiple implantable devices which have been deployed within the body (e.g., pace maker, pump, defibrillator, etc.). The controller is configured to monitor a fuel gauge or available energy level of the battery by communicating with the implanted system. Based on information provided to the controller, the implanted power supply can begin charging or charge on demand. The controller can be set by the user or the operator to charge on set schedules or based on energy storage level of the implanted power supply.

Figure 25:
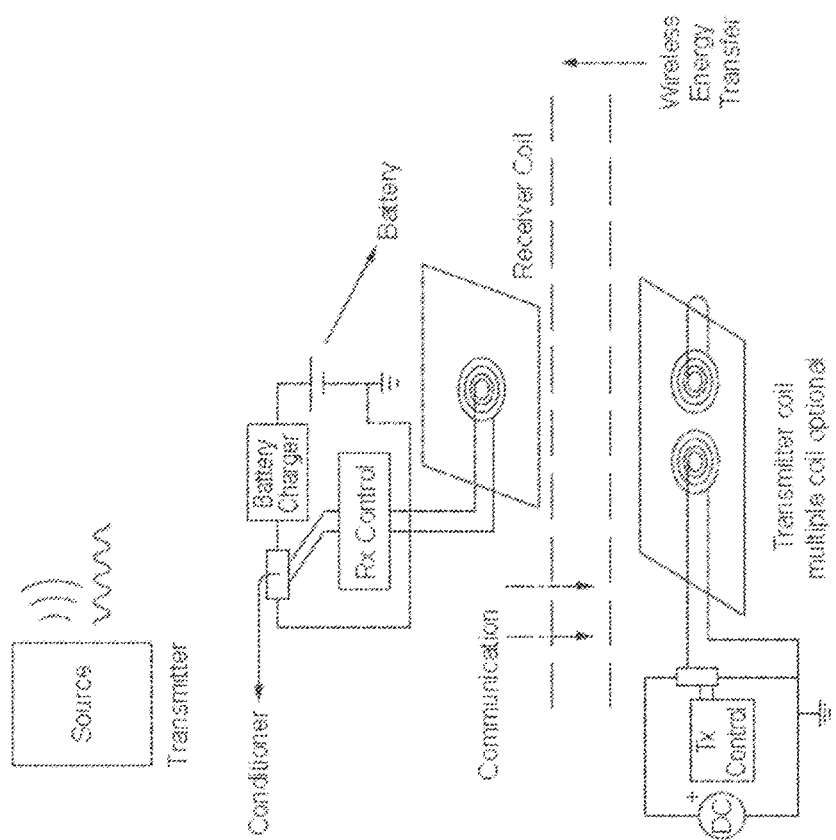
FIG. 25 is a block diagram that illustrates additional details of the wireless charging system shown in FIG. 24.

FIG. 25 is a block diagram that illustrates additional details of the wireless charging system 800. The external system 800 provides for an improved configuration for wireless power transfer for biological applications by use of magnetic resonance, as described herein. In some embodiments, the external system can transmit sufficient power to charge a battery (e.g., the battery contained within the internal power supply, of the types described herein). The magnetic resonance charging can be activated by a user from outside of the body, by a power supply or implanted device signaling the power supply to get activated when the low energy storage level is sensed. To re-charge the power supply for the pump once the pump has been implanted, a wireless charger is brought into proximity to the exterior of the chest wall of a patient. As will be appreciated by those skilled in the art, magnetic resonance charging (or wireless charging) uses an electromagnetic field to transfer energy between two objects as shown in FIGS. 21-25. Energy is conveyed through magnetic resonance coupling to an electrical device, which then uses that energy to charge the device battery.

Although the blood pump assemblies have been shown and described here as including an implanted (also referred to as internal) power supply that is coupled within the target blood vessel, in other embodiments, any of the pump assemblies (and methods) described herein can include an implanted blood pump that is coupled to a power supply implanted within the body, but outside of the heart or the target blood vessel. For example, in some embodiments, the blood pump assembly 100 or 400 (or any other blood pump assemblies described herein) can include a blood pump coupled within the ascending aorta that is electrically coupled to a power supply that is implanted within the body, but outside of the heart, the aorta, or the like. For example, in some embodiments, a blood pump assembly can include a power supply that is superficially mounted (e.g., in a subclavicular region) of the body. In such embodiments, an electrical lead can be routed within the body to couple the blood pump and the power supply.

In some embodiments, such blood pump assemblies can include an electrical lead that is advanced transseptally through the right portion of the heart and into the left ventricle, where it is then coupled to a blood pump implanted within the ascending aorta. The blood pump can be implanted within the ascending aorta in accordance with any of the methods and systems described herein.

Figure 26:
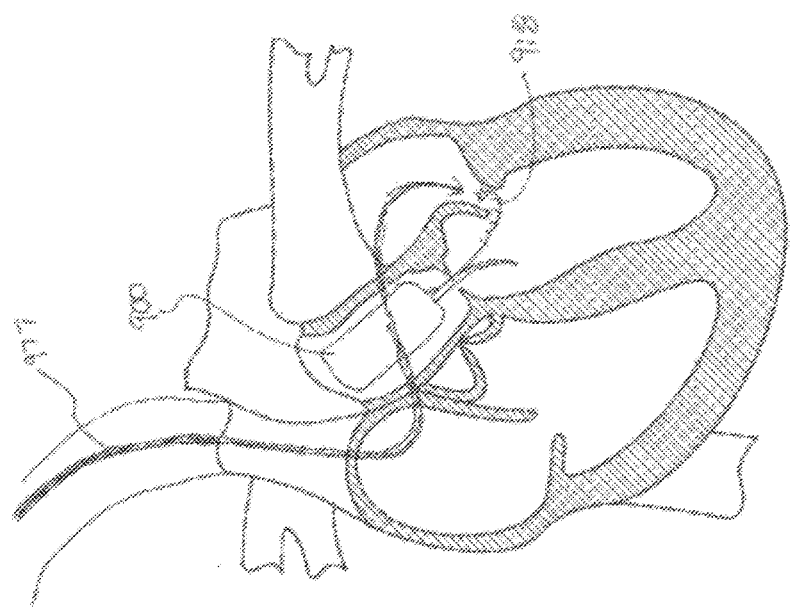
FIG. 26 is a schematic illustration showing a method of retrieving an electrical lead from an intracardiac blood pump assembly, according to an embodiment.
Figure 27:
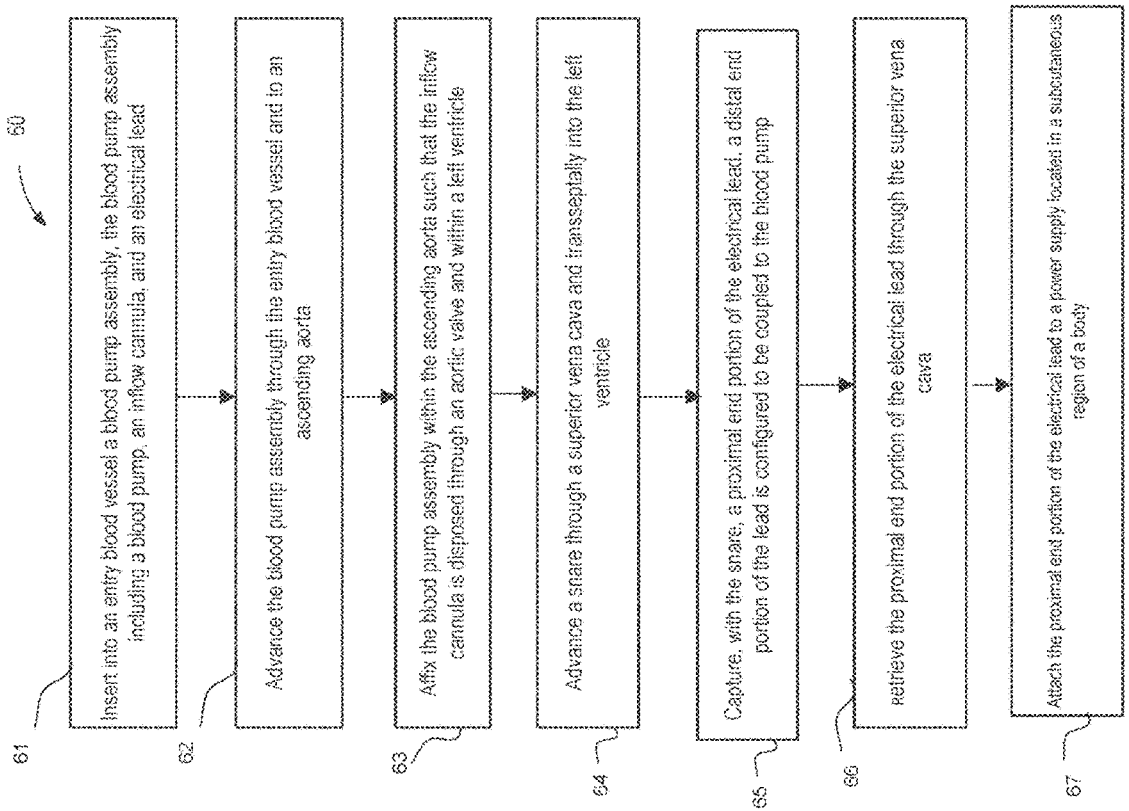
FIG. 27 is a flow chart of a method of retrieving an electrical lead from an intracardiac blood pump assembly, according to an embodiment.

In some embodiments, a method includes routing an electrical lead from a power supply and transseptally into the left side of the heart. For example, FIG. 26 is a schematic illustration of and FIG. 27 is a flow chart illustrating a method 60 of coupling an electrical lead between an implanted extracardiac power supply and an intracardiac pump assembly, according to an embodiment. The method 60 can performed using any of the blood pump assemblies described herein. Although the schematic illustration in FIG. 26 shows a blood pump 900 having an electrical lead 918 that is retrieved using a snare 977, the method can be performed using any of the blood pump assemblies described herein.

The method 60 includes inserting into an entry blood vessel a blood pump assembly, at 61. The blood pump assembly including a blood pump, an inflow cannula, and an electrical lead. The blood pump assembly is then advanced through the entry blood vessel and to an ascending aorta, at 62. The blood pump assembly is affixed within the ascending aorta such that the inflow cannula is disposed through an aortic valve and within a left ventricle, at 63. The implanting and affixing of the blood pump assembly can be performed according to any of the methods described herein. For example, in some embodiments, the method 60 includes implanting and affixing a blood pump assembly that includes an expandable member (not shown in FIG. 26).

A snare is then advanced through a superior vena cava and transseptally into the left ventricle, at 64. This is shown in FIG. 26 by the snare 977, which advances transseptally as shown by the arrow at the end of the snare. A proximal end portion of the electrical lead is then captured using the snare, at 65. As shown in FIG. 26, a distal end portion of the lead is configured to be coupled to the blood pump. The proximal end portion of the electrical lead is then advanced through the superior vena cava, at 66. The method further includes attaching the proximal end portion of the electrical lead to a power supply located in a subcutaneous region of a body, at 67.

Figure 28:
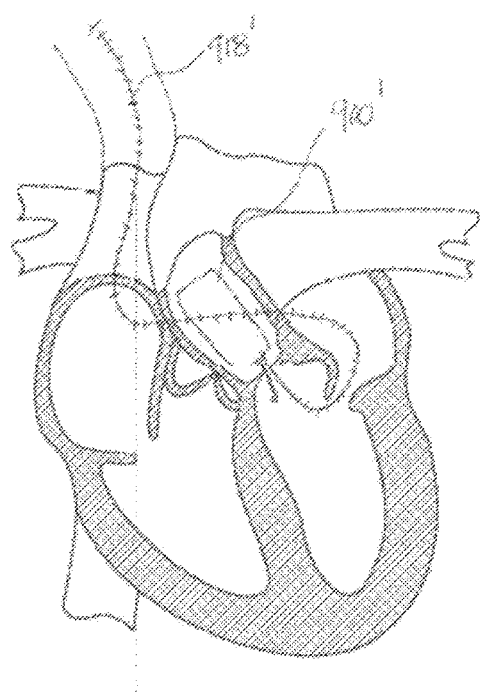
FIGS. 28 and 29 are schematic illustrations showing a method of routing and coupling an electrical lead to an intracardiac blood pump assembly, according to an embodiment.
Figure 29:
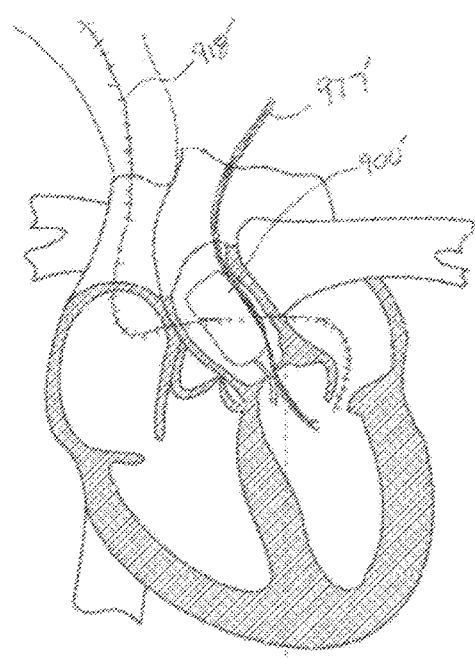
Figure 30:
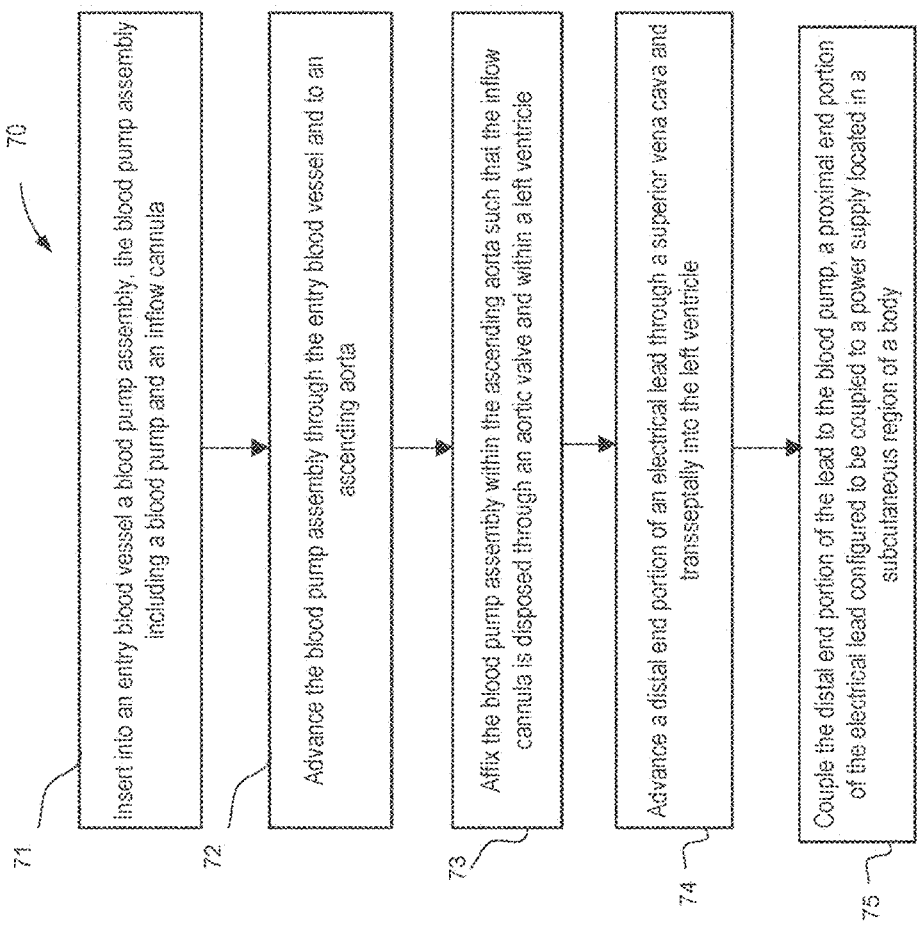
FIG. 30 is a flow chart of a method of routing and coupling an electrical lead to an intracardiac blood pump assembly, according to an embodiment.

Although the method 60 is shown as implanting the pump assembly with the electrical lead attached thereto, and then routing the lead back to the power supply, in other embodiments, the pump assembly can be implanted without the electrical lead, and the lead can be routed transseptally into the left ventricle and then coupled to the pump assembly. For example, FIGS. 28 and 29 are schematic illustrations of and FIG. 30 is a flow chart illustrating a method 70 of coupling an electrical lead between an implanted extracardiac power supply and an intracardiac pump assembly, according to an embodiment. The method 70 can performed using any of the blood pump assemblies described herein. Although the schematic illustration in FIGS. 28 and 29 shows a blood pump 901' having an electrical lead 918' that is manipulated and attached using a snare 977', the method can be performed using any of the blood pump assemblies described herein.

The method 70 includes inserting into an entry blood vessel a blood pump assembly, at 71. The blood pump assembly including a blood pump and an inflow cannula. The blood pump assembly is then advanced through the entry blood vessel and to an ascending aorta, at 72. The blood pump assembly is affixed within the ascending aorta such that the inflow cannula is disposed through an aortic valve and within a left ventricle, at 73. The implanting and affixing of the blood pump assembly can be performed according to any of the methods described herein. For example, in some embodiments, the method 70 includes implanting and affixing a blood pump assembly that includes an expandable member (not shown in FIGS. 28 and 29).

A distal end portion of an electrical lead through a superior vena cava and transseptally into the left ventricle snare is then advanced through a superior vena cava and transseptally into the left ventricle, at 74. The distal end portion of the electrical lead is then coupled to the blood pump, at 75. The proximal end portion of the electrical lead is configured to be coupled to a power supply located in a subcutaneous region of a body.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, in some embodiments, any of the expandable members shown and described herein can include a marker portion (e.g., a marker band) configured to allow the practitioner to visualize the position of the expandable member within the blood vessel. Similarly, in some embodiments, any of the blood pumps, inflow cannulas, and electrical leads described herein can include a marker portion. In the manner, the practitioner can visualize the position of the components of the blood pump assembly to ensure the appropriate placement within the body. The marker portions can include any a radiopaque material, such as platinum.

Although shown and described as including a set of flexible segments, in other embodiments, the expandable member 151 (and any of the expandable members shown and described herein) can be monolithically constructed from a material sheet that is fabricated to include a series of pores, and that can transition from the collapsed configuration to the expanded configuration. For example, in some embodiments, any of the expandable members described herein can be a laser-cut expandable member.

For example, any of the expandable members described herein can be constructed from any suitable material or combination of different materials disclosed herein. Moreover, in some embodiments, at least a portion of any of the expandable members described herein (e.g., the expandable members 151, 251, 351, 451 and 551) can be coated. Such coatings can include, for example, a drug coating.

Any of the blood pump assemblies described herein can include one or more sensors to measure the cardiac output and activity level of the patient. Such sensors can include, for example, a flow sensor, an accelerometer, or the like. Moreover, any of the blood pump assemblies described herein can include a control system configured to receive one or more signals from the sensor(s) and adjust the output of the blood pump based on such signals. For example, any of these devices may include one or more sensors on or in the pump (e.g., within the pump housing) including one or more sensors to detect and/or determine cardiac output, oxygen saturation, blood pressure, pulse rate and/or activity level. These one or more sensors may be used as feedback to adjust the cardiac output based on these parameters and/or based on physician instructions.

For example, in some variations the pump or stent (or both) may include one or more sensors to determine cardiac output, e.g., by detecting one or more indicators of stroke volume and/or heart rate. Heart rate may be determined electrically (e.g., using a sensor detecting ECG data (including one lead ECG, measured from within or on the heart) or electromechanically (e.g., using a sensor to determine heartbeat and therefore heart rate). The stroke volume, or a proxy for stroke volume (including just heart rate) may be determined either in the pump or external to the pump, and feedback control may be generated and provided to the pump to modify its operation. The feedback control may be locally generated (e.g., within the pump itself, in a closed-loop manner) or externally and transmitted to the pump.

In some embodiments, any of the blood pump assemblies described herein include a close-coupled (or internally mounted) power supply that can be recharged and/or powered by any suitable wireless method, such as, for example, by inductive coupling, capacitive coupling, or the like. Moreover, although the system 800 described above is shown as including one external transmission portion that is coupled to one internal power supply (e.g., within or closely-coupled to the blood pump), in other embodiments, any of the blood pump assemblies or systems described herein can include any number of intermediate structures to facilitate the desired power transfer. For example, in some embodiments, any of the blood pump assemblies described herein can include an external power supply, an internal receiving member (e.g., a pad, harvesting device, or the like) that is subcutaneously mounted, and an internal power supply (e.g., that is within or closely-coupled to the blood pump). In such embodiments, the internal receiving member can be mounted in the subclavicular region, and can be coupled to the power supply of a blood pump mounted within the ascending aorta via an electrical lead. In some embodiments, the electrical lead can be routed to the power supply of the blood pump transseptally according to the method 60 or the method 70 described herein.

Although the blood pump assemblies described herein include a close-coupled (or internally mounted) power supply that can be charged via inductive coupling and a magnetic field, in some embodiments, any of the assemblies described herein can be charged and/or powered via radiofrequency (RF) charging, with the ability to harvest energy by receiving via antenna on the device.

Although various embodiments have been described as having particular features and/or combinations of components, other embodiments are possible having a combination of any features and/or components from any of embodiments where appropriate. For example, any of the expandable members shown and described herein can be constructed from any of the materials described herein with respect to any other expandable member. Specifically, any of the expandable members described herein can be constructed from any suitable material that provides the desired strength, spring characteristics and biocompatibility. For example, in some embodiments, any of the expandable members described herein can be constructed from a metal, such as, for example, a medical grade stainless steel, a cobalt-based alloy, platinum, gold, titanium, tantalum, and/or niobium. In some embodiments, any of the expandable members described herein can be constructed from a shape memory material, such as a nickel-titanium alloy (e.g., Nitinol®). In other embodiments, any of the expandable members described herein) can be constructed from a polymeric material, such as, for example, poly(L-lactide) (PLLA), poly(D,L-lactide) (PLA), poly(glycolide) (PGA), poly(L-lactide-co-D,L-lactide) (PLLA/PLA), polyethylene terephthalate (PET), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene)poly(D,L-lactide-co-caprolactone) PLA/PCL), poly(glycolide-co-caprolactone) (PGA/PCL), poly(phosphate ester), or the like.

Any of the struts described herein can be constructed from any suitable material that provides the desired strength to suspend the blood pump and/or power supply within a blood vessel. Moreover, any of the struts described herein can be flexible and can change their length and/or orientation to allow the expandable member to transition from the collapsed configuration to the expanded configuration. For example, any of the struts described herein can be constructed from a metallic material, such as, a medical grade stainless steel. In other embodiments, any of the struts described herein can be constructed from a shape memory material, such as a nickel-titanium alloy (e.g., Nitinol®). In other embodiments, any of the struts described herein can be constructed from a polymeric material, such as, for example, poly(L-lactide) (PLLA), poly(D,L-lactide) (PLA), poly(glycolide) (PGA), poly(L-lactide-co-D,L-lactide) (PLLA/PLA), polyethylene terephthalate (PET), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester), or the like.

Figure 31A:
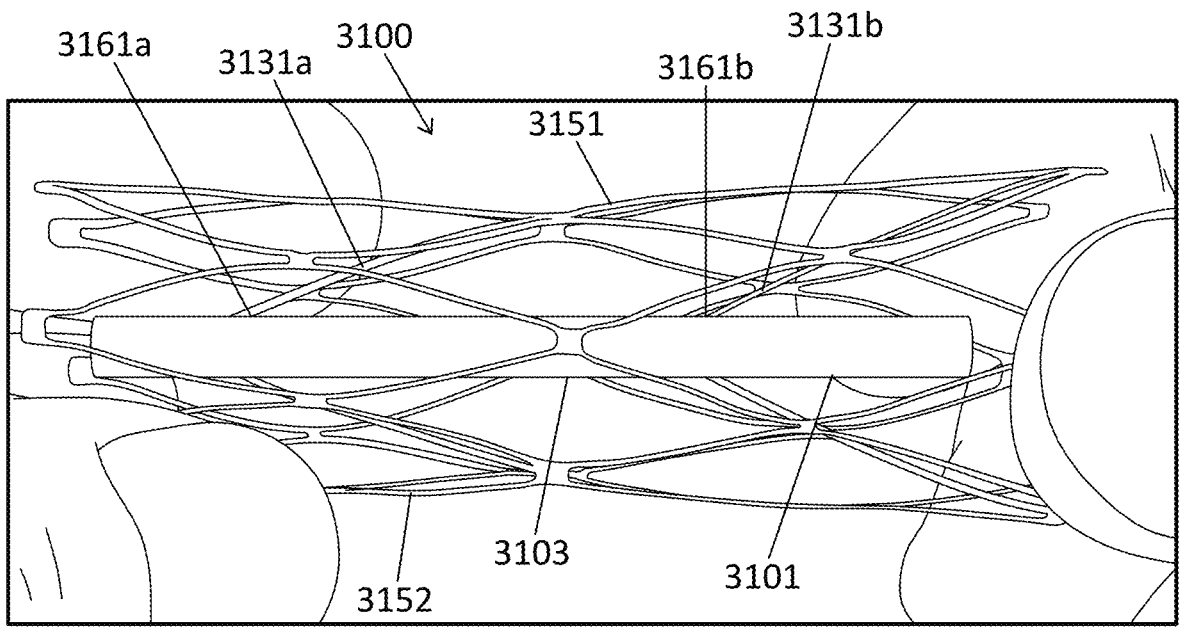
FIGS. 31A-31F illustrate an exemplary blood pump assembly having a detachable stent.
Figure 31B:
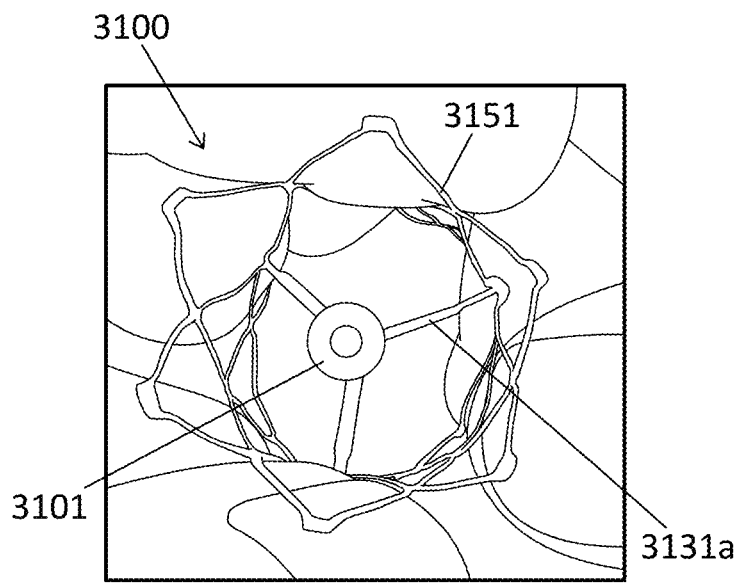

As mentioned above, in some examples the expandable member (stent) includes one or more struts that are configured to remain attached to the expandable member after detaching from the blood pump. FIGS. 31A-31F illustrate an example of a blood pump assembly 3100 with such a detachable stent 3151. FIG. 31A shows a side view and FIG. 31B shows a frontal view of the blood pump assembly 3100, where the blood pump 3101 is attached to the stent 3151 in an expanded configuration. The blood pump 3101 can include any of the blood pumps described herein. For example, the blood pump 3101 (and any of the blood pumps described herein) can include a pumping unit (e.g., an impeller, a roller and/or a balloon) enclosed within a housing 3103. The blood pump assembly 3100 may include an inflow cannula and an electrical lead, as described herein.

The stent 3151 can include a network of flexible segments 3152 that together are configured to collapse radially inward toward the blood pump 3101. The blood pump assembly 3100 can be maneuvered within the patient's vessel while in the collapsed configuration (e.g., within a delivery catheter and/or sheath), then expanded to the expanded configuration once positioned at a target location within the patient. When expanded, the outer surface of the stent 3151 may contact the inner surface of a blood vessel. The flexible segments 3152 can form a tubular wall that defines an interior volume for the blood pump 3101 to pump blood therethrough. Unless the pump is attached to the expandable member, in some examples the inner lumen of the expandable member may be open, without any projections into the lumen.

The stent 3151 includes struts 3131a and 3131b (also referred to herein as "arms") that can be configured to extend radially inward with respect to the tubular wall formed by the segments 3152 of the stent 3151. Distal ends of the arms 3131a/3131b can be configured to removably couple to corresponding attachment portions (e.g., attachment sites) 3161a/3161b of an outer housing 3103 of the blood pump 3101 to support the blood pump 3101 within the interior volume of the stent 3151, as shown in FIGS. 31A and 31B. The stent 3151 may include sets of arms 3131a/3131b along different longitudinal portions of the stent 3151 to securely support the blood pump 3101 in place. In this case, a first set of arms 3131a is positioned along a first longitudinal portion (e.g., distal portion) of the stent 3151, and a second set of arms 3131b is positioned along a second longitudinal portion (e.g., proximal portion) of the stent 3151. Each set of arms 3131a/3131b may include multiple individual arms. In this case, the first set of arms 3131a and the second set of arms 3131b each includes three arms. In some cases, the arms in each set of arms 3131a/3131b are arranged radially equidistant with respect to each other to provide consistent radial support for the blood pump 3101. In this case, the arms 3131a/3131b are configured to support the blood pump 3101 at a substantially central position within the stent 3151.

The arms 3131a/3131b may be made of a flexible material so that they can bend radially inward to attach to the blood pump 3101. In some cases, the arms 3131a/3131b are made of a shape memory material, such as a shape memory alloy (e.g., nitinol). In some cases, the arms 3131a/3131b are made of the same material as the segments 3152 of the stent 3151. In some cases, the arms 3131a/3131b are made of a magnetically attractive material or a magnetic material. In some examples, the arms may be made of a stainless steel material.

The blood pump assembly may be inserted into the target location within the body with the pump attached (removably attached) to the expandable member, so that the expandable member is collapsed over the pump; alternatively in some examples the pump may be inserted and coupled to the expandable member after the expandable member is already in position. In any of these apparatuses, the pump may be removed from the expandable member, leaving one or more of the struts (e.g., arms) that flexibly connect the pump to the expandable member to retract back against the lumen (so that they are in-line with the long axis of the expandable member and otherwise out of the way).

Figure 31C:
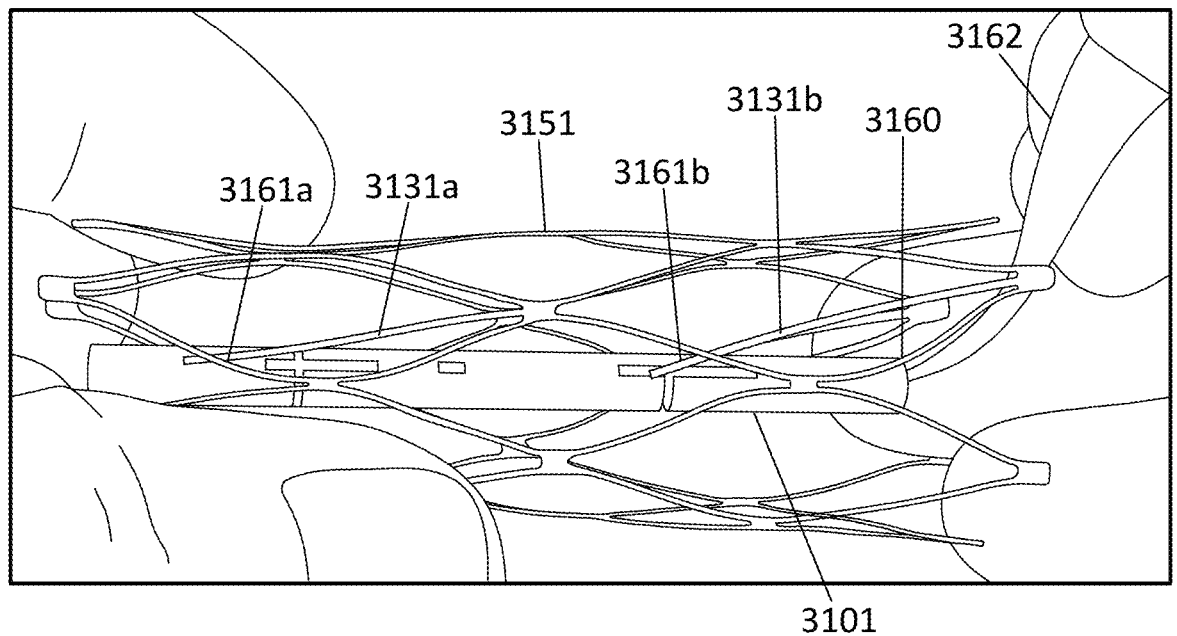
Figure 31D:
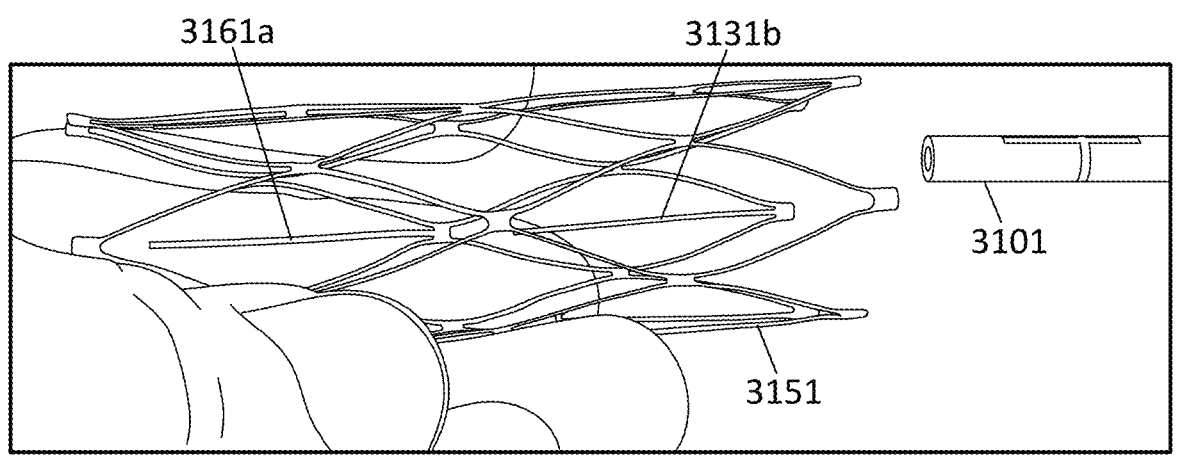

FIGS. 31C and 31D illustrate how the blood pump 3101 may be decoupled from the stent 3151 according to some embodiments. The attachment portions 3161a/3161b of the blood pump 3101 may include openings within the housing 3103 of the blood pump 3101. The distal ends of the arms 3131a/3131b may fit within openings in the housing 3103 of the pump and/or between the housing 3103 and an inner retention member within the housing 3103. In some cases, the inner retention member is a tube or cylinder having a diameter sufficiently small outer diameter to fit within the housing 3103 and a sufficiently large outer diameter to create a retention force (e.g., by friction) against the distal ends of the arms 3131a/3131b to retain the arms 3131a/3131b coupled to the blood pump 3101. In some cases, the inner retention member may be magnetic (or be magnetically attractive). Magnetic force between the ends of the struts (arms) and the attachment portion(s) of the pump may help attached/retain the pump coupled to the struts and therefore the expandable member.

FIG. 31C shows a tool 3162 being used to decouple the arms 3131a/3131b from the blood pump 3101. In this case, the tool 3162 is used to translate (e.g., push) the inner retention member (e.g., inner tube) with respect to the housing 3103 such that the distal ends of the arms 3131a/3131b are released from between the outer housing 3103 and the inner retention member, thereby causing the distal ends of the arms 3131a/3131b to pass out of the openings within the housing 3103.

Alternatively, in some examples the arms, which are integral to the expandable member, may be configure to removably couple with the blood pump housing via attachment portions on the blood pump housing. The attachment portions may include a slot, which may be configured as described above, and/or opening into the housing or a projection on the outer surface of the blood pump housing. The attachment portions on the blood pump may be configured similarly to those described above for the expandable member.

FIG. 31D shows the blood pump 3101 being removed from the internal volume of the stent 3151. The arms 3131a/3131b may have a pre-formed shape that extends in parallel to the long axis of the stent 3151. Thus, once the arms 3131a/3131b are released from the attachment portions 3161a/3161b, the arms 3131a/3131b can (in some variations) spring back to align with the long axis of the stent 3151. That is, the arms 3131a/3131b may bend radially outward and in radial alignment with the tubular shape of the stent 3151 after the arms 3131a/3131b are released from the pump 3101. This can allow for easier removal of the pump 3101. This may also prevent the arms from projecting into (and occluding) the pathway through the expandable member (e.g., stent), which may be beneficial.

Figure 31E:
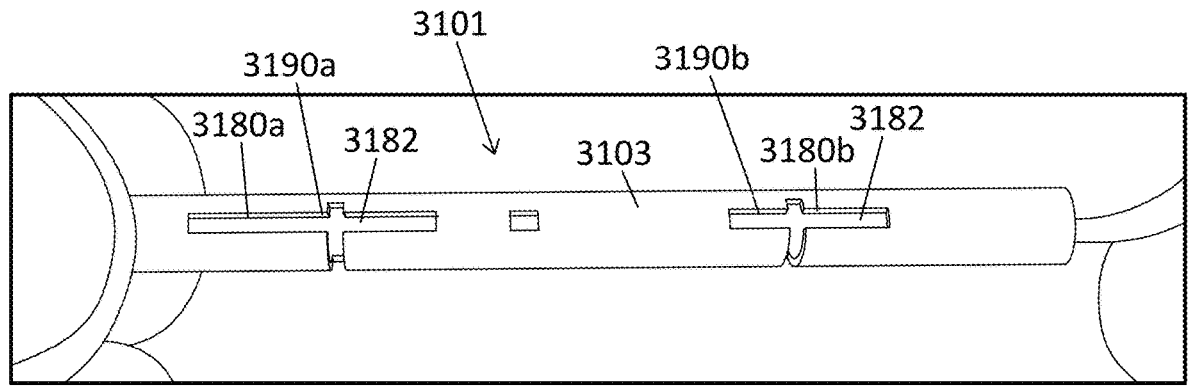

FIG. 31E illustrates the blood pump 3101, showing the openings 3180a/3180b within the housing 3103 and portions of the (optional) inner retention member 3182 within the housing 3103. As shown, in some examples housing may include a notch 3190a/3190b at each opening 3180a/3180b that is configured to accept attachment members as distal ends of the arms 3131a/3131b of the stent 3151. In some examples, in which an inner retention member is included, the notch may be part of the inner retention member 3182, or at least partially into the inner retention member, to allow the inner retention member to apply force to reliably secure the arms (and in particular, the distal ends of the arms, which may be adapted to engage the notch region).

Figure 31F:
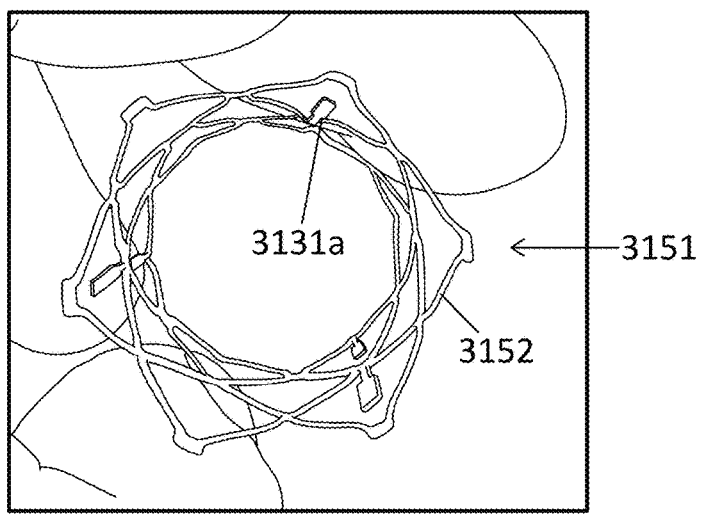

FIG. 31F shows the stent 3151 decoupled from the blood pump 3101. As shown, the arms 3131a are in radial alignment with the tubular shape of the stent 3151. Thus, the arms 3131a can form the tubular shape of the stent 3151 along with the segments 3152. In this case, the arms 3131a are parallel with respect to a central axis of the stent 3151.

In some examples, struts (e.g., arms) may extend from both the expandable member (e.g., stent) and from the blood pump, as described above. Thus, the blood pump may include one or more struts (e.g., arms) as described above in FIGS. 9-13 and 16 or other examples, to engage attachment portions on the expandable member, and one or more struts (arms) on the expandable member may be configured to engage attachment portions on the blood pump.

Figure 32A:
FIGS. 32A and 32B illustrate exemplary attachment members for removably attaching a stent to a blood pump.
Figure 32B:
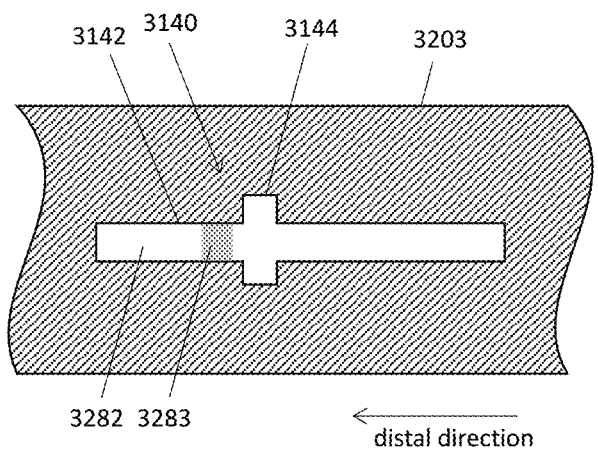

FIGS. 32A and 32B illustrates exemplary attachment members for removably attaching a stent to a blood pump. FIG. 32A illustrates an exemplary attachment member 3230 (configured as an attachment member) at a distal end of an arm 3231 of a stent. In this case, the attachment member (attachment member) 3230 includes wide distal end of the arm 3231 forming a "T" shape. FIG. 32B illustrates an exemplary attachment portion 3240 at in a housing 3203 of the blood pump. In this case, the attachment portion 3240 includes a slotted opening having a longitudinal section 3142 that is parallel to the longitudinal axis of the blood pump, and a transverse section 3144 that is transverse to the longitudinal axis of the blood pump (optionally, the travers section may be at an angle, e.g., between 34-90 degrees relative to the long axis of the pump). The transverse section 3144 of the opening 3240 may have a width that is at least as wide as the T-shaped attachment member 3230 of the arm 3231 so that the T-shaped attachment member 3230 can fit within the transverse section 3144 of the opening 3240.

To engage the arm 3231 with the housing 3203, the arm 3231 can be bent radially inward with respect to the stent from a straight shape to a curved shape and positioned with the transverse section 3144 of the opening 3240. The arm 3231 (which is, in this example, integrally formed as part of the expandable member) can be translated relative to the blood pump housing 3203 (or the blood pump housing 3203 can be translated relative to the arm 3231) to move the head of the attachment member, in this example a T-shaped attachment member 3230, into the attachment portion of the body of the blood pump. In some examples, the attachment member of the strut (e.g., arm) may be inserted into and/or under a narrower longitudinal section 3142 of the opening 3240. For example, the stent can be pushed in a distal direction relative to the blood pump to force the attachment member 3230 under a distal portion of the longitudinal section 3142 section of the opening 3240. In this example, the T-shaped attachment member (attachment member) 3230 can be positioned between the housing 3203 and an inner retention member 3282 within the housing 3203 forming the attachment portion of the pump. In general, the attachment portion mates with an attachment member. In some examples, the blood pump may include an inner retention member 3282 behind the outer housing of the blood pump that can accepts the T-shaped attachment member 3230. In some cases, the inner retention member 3282 includes a notch 3283 region that is configured to accept the widened head region of the attachment member. In some examples the blood pump (e.g., an inner retention member) can provide a magnetic force to retain the attachment member 3230 within the opening 3240 of the housing 3203.

To decouple the housing 3203 (and the blood pump) from the arm 3231 (and the stent), the arm 3231 can be translated relative to the blood pump housing 3203 in the opposite direction (or the blood pump housing 3203 can be translated relative to the arm 3231 in the opposite direction) to move the T-shaped attachment member 3230 (e.g., attachment member) from under the narrower longitudinal section 3142 to the transverse section 3144 of the opening 3140. For example, the stent can be pulled in a proximal direction relative to the blood pump to force the T-shaped attachment member 3230 (e.g., attachment member) toward the transverse section 3144 section of the opening 3140. Once the T-shaped attachment member 3230 reaches the transverse section 3144 of the opening 3140, the arm 3231 can move radially outward and return to its straight shape in radial alignment with the circumference of the stent.

Figure 33A:
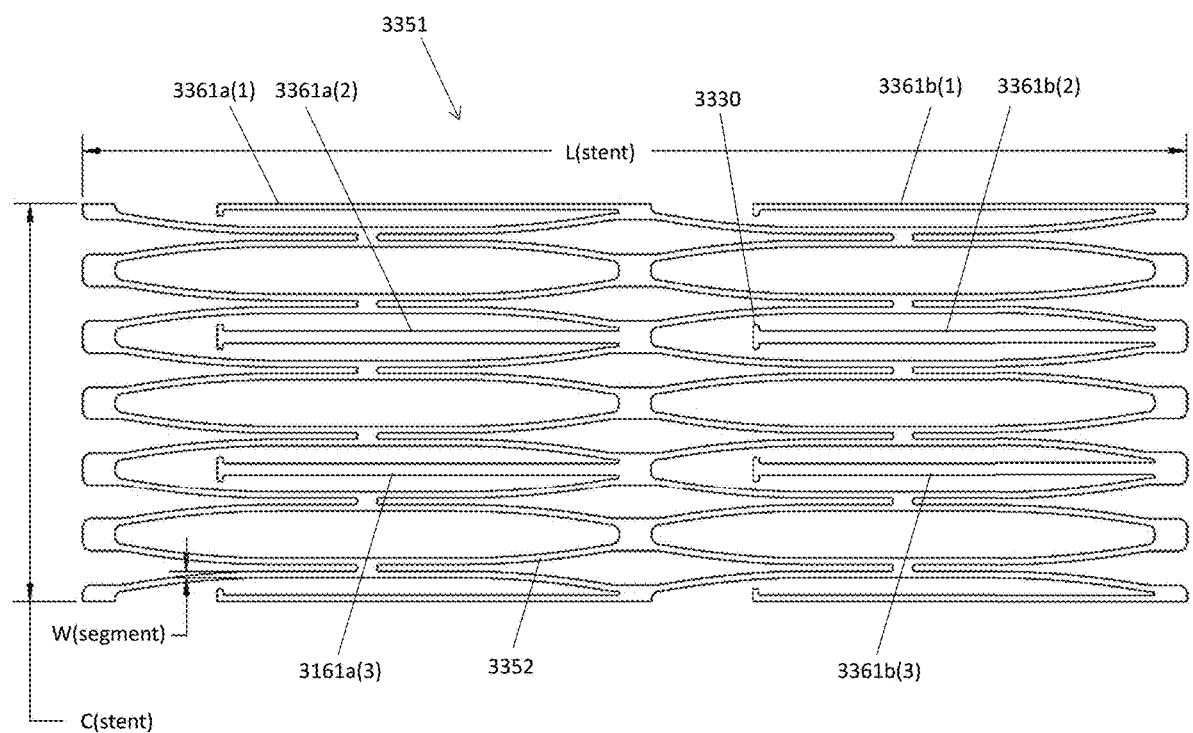
FIGS. 33A and 33B illustrate flattened views of an exemplary stent and blood pump housing, respectively, which include attachment members for removably attaching the stent to the blood pump housing.

FIG. 33A illustrates a flattened view of an exemplary stent 3351. The stent may be made from a tube of shape memory material (e.g., nitinol). In some cases, the stent pattern is laser cut into the tube of shape memory material. The stent 3351 includes a pattern of flexible segments 3352 that form the collapsible/expandable stent frame structure. The width W(segment) of the narrowest portions of the flexible segments 3352 may vary depending on desired expansion/collapse forces and other factors. In some examples, the width W(segment) may range from about 0.010 to about 0.020 inches. In some examples, a length L(stent) of the stent 3351 may range from about 2.0 inches to about 3.0 inches. In some examples, a circumference C(stent) may range from about 0.8 inches to about 1.1 inches.

In this example, the stent 3351 includes a first set of arms 3361*a*(1)-3361*a*(3) at a first longitudinal portion of the stent 3351, and a second set of arms 3361*b*(1)-3361*b*(3) at a second longitudinal portion of the stent 3351, for a total of six arms 3361*a*/3361*b*. However, the stents described herein can include any number of sets of arms (e.g., 1, 2, 3, 4, 5, 6, 7, 8, 9, 10, or more) and any total number arms (e.g., 1, 2, 3, 4, 5, 6, 7, 8, 9, 10, 12, 14, 15, 16, 18, 20, or more). The distal ends of the arms 3361*a*/3361*b* include attachment members 3330 that are configured to engage with corresponding attachment members of the blood pump. In this case, the attachment members 3330 are T-shaped distal ends of the arms 3361*a*/3361*b*. However, the attachment members of the arms for the stents described herein can have any suitable shape (e.g., circular, elliptical, square, triangular, etc.).

As described herein, the stent 3351 may be made of a shape-memory alloy. The shape-memory alloy may be heat-set to have a pre-deformed (remembered) shape where the arms 3361*a*/3361*b* are in radial alignment with the flexible segments 3352 to form the tubular shape of the stent 3351. The arms 3361*a*/3361*b* may have a straight pre-deformed (remembered) shape.

Figure 33B:
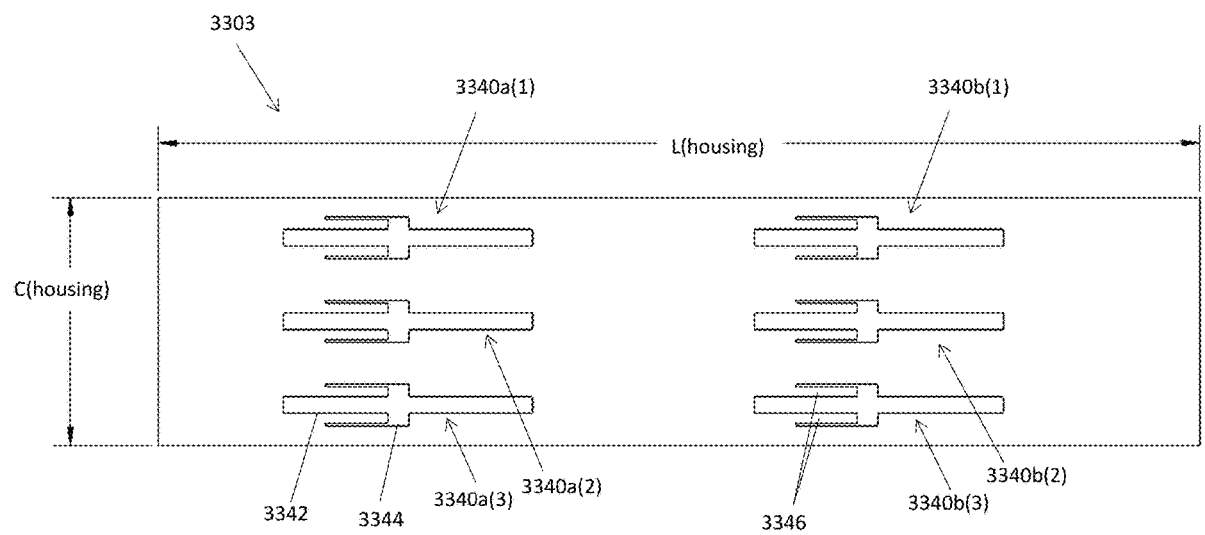

FIG. 33B illustrates a flattened view of an exemplary housing 3303 of a blood pump that is configured to mate with the stent 3351 of FIG. 33A. The housing 3303 may made of any material(s). In some examples, the housing 3303 may be made from a tube of shape memory material (e.g., nitinol) with (e.g., laser) cut pattern of openings. The circumference C(housing) of the housing 3303 may vary depending on the size and shape of the blood pump. In some examples, the housing circumference C(housing) may range from about 0.4 inches to about 0.8 inches. In some cases, the length L(housing) of the housing 3303 may be less than the length L(stent) of the stent 3351. In some examples, the housing length L(housing) may range from about 2.0 inches to about 3.0 inches.

The housing 3303 can include openings 3340*a*/3340*b* positioned on the housing 3303 to mate with corresponding attachment members 3330 of the arms 3361*a*/3361*b* of the stent 3351. In this example, the housing 3303 includes a first set of openings 3340*a*(1)-3340*a*(3) at a first longitudinal portion of the housing 3303, and a second set of openings 3340*b*(1)-3340*b*(3) at a second longitudinal portion of the housing 3303, for a total of six openings 3340*a*/3340*b*. However, the blood pump housings described herein can include any number of sets of openings (e.g., 1, 2, 3, 4, 5, 6, 7, 8, 9, 10, or more) and any total number openings (e.g., 1, 2, 3, 4, 5, 6, 7, 8, 9, 10, 12, 14, 15, 16, 18, 20, or more).

Each of the openings includes a longitudinal section 3342 that is parallel to the longitudinal axis of the housing 3303, and a transverse section 3344 that is transverse to the longitudinal axis of the housing 3303. The transverse section 3344 is wide enough to allow an attachment members 3330 of a corresponding arm 3361*a*/3361*b* to fit within the corresponding opening 3340*a*/3340*b*. Translation of the arm 3361*a*/3361*b* relative to the housing 3303 can slide the attachment members 3330 under the longitudinal section 3342 and capture the attachment member 3330 between the housing 3303 and an underlying inner retention member, as described herein. In this case, the longitudinal section 3342 includes tabs 3346 that are configured to flare slightly outward, thereby allowing the attachment member 3330 to fit under the housing 3303.

Figure 34:
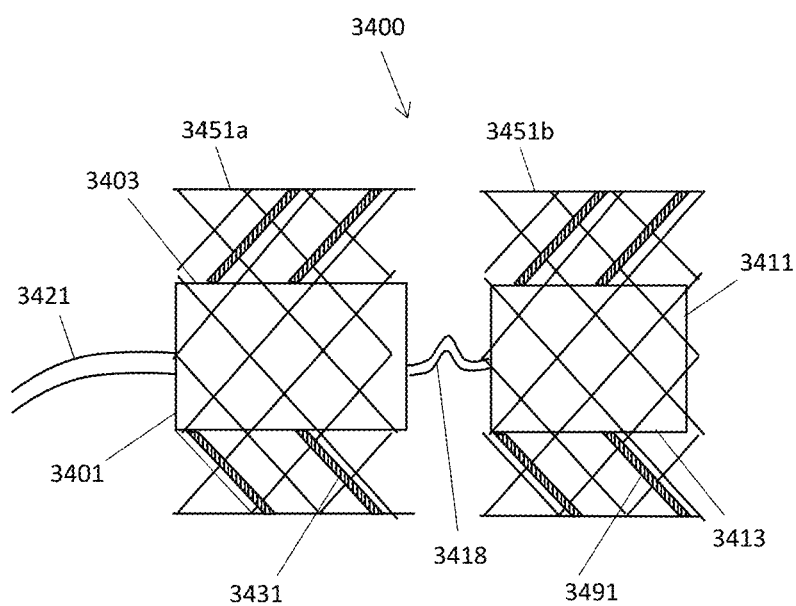
FIG. 34 illustrates an exemplary blood pump assembly having any of detachable stent features of FIGS. 31A-33B, where the assembly includes a separate blood pump and power supply.

In some cases, the blood pump has an integrated power supply (e.g., battery) that is disposed within the same housing as the blood pump. In other cases, the blood pump is coupled to a separate power supply. FIG. 34 shows an exemplary blood pump assembly 3400 having a separate blood pump 3401 and power supply (e.g., battery) 3411. The blood pump assembly 3400 can include a first stent 3451*a* for supporting the blood pump 3401 and a second stent 3451*b* for supporting the power supply 3411. An inflow cannula 3421 may be coupled to the blood pump 3401. The power supply 3411 can be coupled to the blood pump 3401 by an electrical lead 3418 such that the blood pump 3401 and the power supply 3401 may be axially aligned. The electrical lead 3418 may be flexible such that the pump 3401 and the power supply 3411 can articulate relative to each other, which may allow for easier advancement through the vasculature (e.g., the aortic arch). The electrical lead 3418 can have any suitable length such that the power supply 3411 is closely coupled to the blood pump 3401, while still maintaining the desired flexibility for implantation. The power supply 3411 can include any suitable components of the types shown and described herein to provide power to the blood pump 3401 within the vasculature. For example, the power supply 3411 may include one or more batteries, a capacitance storage system, and/or a charging module (e.g., that can be electromagnetically coupled to an external power supply).

The blood pump 3401 and/or the power supply 3411 may be detachably coupled to their respective stents 3451*a* and 3451*b* using any of the attachment members described with respect to FIGS. 31A-33B. For example, the first stent 3451*a* may include fixedly attached arms 3431 that include distal ends having attachment members that are configured to detachably couple to attachment portions of the housing 3403 of the blood pump 3401. Likewise, the second stent 3451*b* may include fixedly attached arms 3491 that include distal ends having attachment members that are configured to detachably couple to attachment portions of the housing 3413 of the power supply 3411. This arrangement may be useful when one of the blood pump 3401 or the power supply 3411 requires removal, e.g., for replacement or repair. One of the blood pump 3401 or the power supply 3411 may be removed from the vasculature while leaving the other (e.g., still functional) component within the vasculature.

Figure 35:
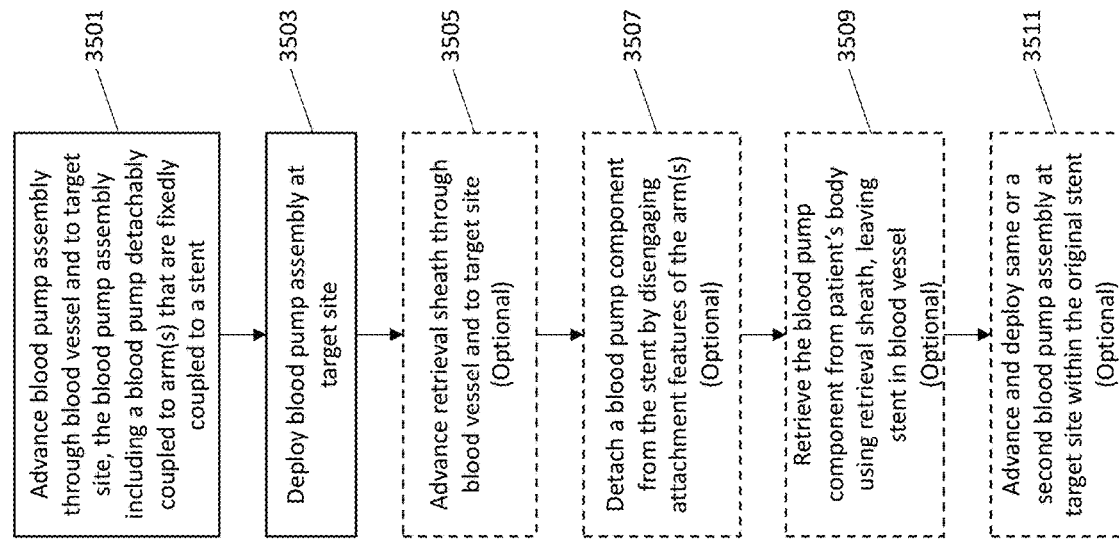
FIG. 35 is a flowchart illustrating an exemplary method of retrieving one or more components of a blood pump assembly, such as the blood pump assemblies of FIGS. 31A-34, from a patient's blood vessel.

The pump assemblies shown in FIGS. 31A-34 are well suited for use when one or more components of the pump assembly that is deployed within a patient's blood vessel requires replacement or repair. FIG. 35 is a flowchart indicating an exemplary method of using the blood pump assemblies of FIGS. 31A-34. At 3501, the blood pump assembly is advanced through the blood vessel to a target deployment site, e.g., within the ascending aorta. The blood pump assembly includes a blood pump having a housing with attachment portion(s) that is/are detachably coupled to strut(s) (e.g., arm(s)) that are coupled to (or integrally formed with) an expandable member (e.g., stent). At 3503, the blood pump assembly (expandable member and pump) is deployed at the target site within the blood vessel. Deployment can include expanding the stent from a collapsed configuration to an expanded configuration. When expanded, flexible segments of the stent can contact the inner surfaced of the blood vessel, thereby anchoring the blood pump assembly to the target site. The stent can form a tubular wall defining an interior volume for the blood pump to pump blood through during operation of the blood pump. In cases where the blood pump assembly includes a separate blood pump and power supply (e.g., FIG. 34), a first stent may support the blood pump and a second stent may support the power supply.

In some cases, it may be desirable to remove the blood pump, but leave the expandable member behind, or to separately remove the blood pump and the expandable member. For example, one or more components of the blood pump may need repair or replacement; the blood pump may need a new battery, or one or more other components of the blood pump may need repair and/or replacement. In such cases, a retrieval procedure can be used to retrieve the blood pump from the patient's body. If the blood pump assembly includes separate blood pump and power supply (e.g., FIG. 34), only one of the blood pump and the power supply may need repair/replacement.

At 3505, a retrieval sheath is optionally advanced through the blood vessel and to the target site. The retrieval sheath (e.g., retrieval sheath 472, FIG. 11) may be positioned around a proximal end portion of a blood pump. At 3507, the blood pump (e.g., blood pump and/or power supply) is optionally detached from the stent by disengaging attachment members of the arm(s). This may be accomplished using a retrieval tool (e.g., retrieval tool 471, FIG. 11) that exerts a force on the blood pump in a distal direction. Since the stent is in contact with the inner surface of the blood vessel, its position can remain securely in place. The applied force on the blood pump can translate the blood pump relative to the stent and arm(s) until the attachment members of the arm(s) are released from openings within a housing of the blood pump, thereby "unlocking" the arm(s) from the blood pump. The arm(s) may be made of a shape memory material that causes the arm(s) to spring back into alignment with the circumference of the stent. That is, the arm(s) can automatically move radially outward and out of the lumen of the stent. As such, the arm(s) may contact the inner surfaces of the blood vessel along with other segments of the stent.

At 3509, once detached, the blood pump (e.g., blood pump and/or power supply) may optionally be placed in the retrieval sheath and retrieved from the blood vessel and out of the patient's body. The stent(s) may be left within the blood vessel at the target site. Since the arm(s) of the stent are out of the interior volume of the stent, they do not block blood flow within the blood vessel. Moreover, since the stent structure is in direct contact with the inner surface of the blood vessel, the stent may have tissue ingrowth and endothelialization. Thus, leaving the stent behind, can reduce the risk of perforation or tearing of the blood vessel by removing the stent.

At 3511, a second (e.g., replacement) pump assembly is optionally advanced and deployed at the target site. The second pump assembly can include a second stent that is expanded within the original stent left within the vasculature. In the case of a separate blood pump and power supply (e.g., FIG. 34), one or both of the blood pump and the power supply may be advanced and deployed into the vasculature. Tissue ingrowth and endothelialization onto the original stent may facilitate the installation of the second pump assembly by providing tissue for the second stent to contact and engage with. After deployment, the second pump assembly may be used to pump blood through the internal volumes of the second stent and the original stent.

Figure 36A:
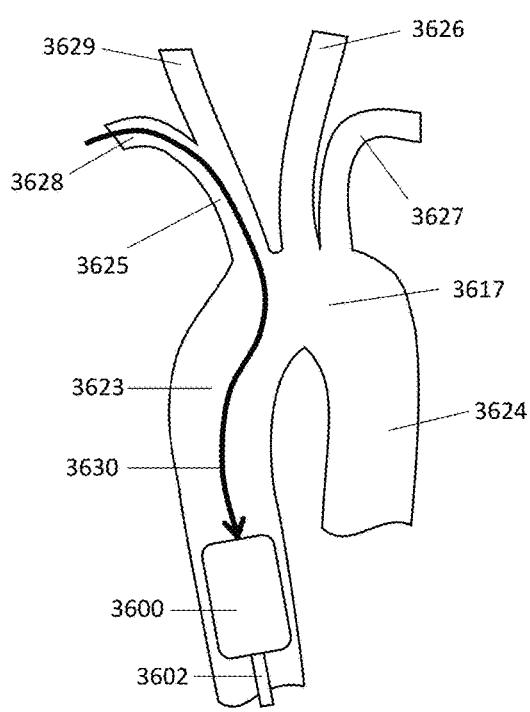
FIGS. 36A and 36B illustrates methods of retrieving an electrical lead from, or routing an electrical lead to, a blood pump assembly within the ascending aorta, according to some embodiments.
Figure 36B:
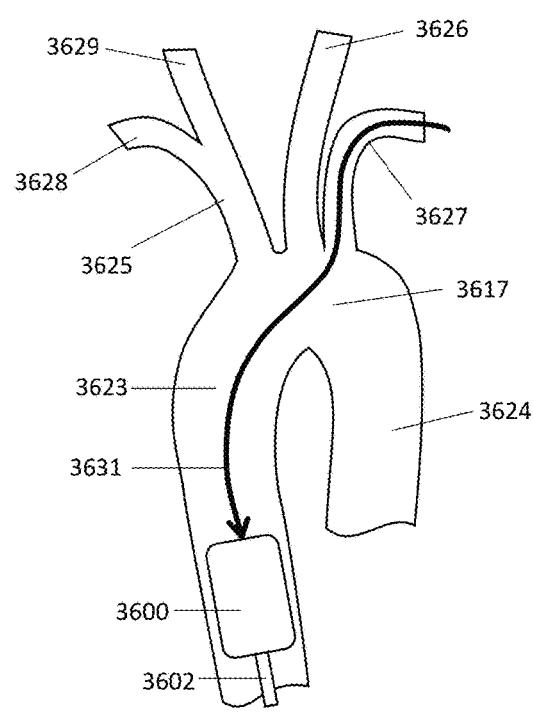

As described herein, in some embodiments, the power supply may be implanted outside of the heart or target blood vessel. In these cases, it may be necessary to retrieve an electrical lead from the blood pump assembly (e.g., FIGS. 26-27) or route an electrical lead to the blood pump assembly (e.g., FIGS. 28-30). FIGS. 36A and 36B illustrates alternative methods of retrieving an electrical lead from, or routing an electrical lead to, a blood pump assembly within the ascending aorta. FIGS. 36A and 36B shows portions of the aorta, including the aortic arch 3617 between the ascending aorta 3623 and the descending aorta 3624. The aortic arch 3617 includes three branches, the brachiocephalic trunk 3625, the left common carotid artery 3626, and the left subclavian artery 3627. The brachiocephalic trunk 3625 divides into the right subclavian artery 3628 and the right common carotid artery 3629. FIG. 36A shows an electrical lead path 3630 that runs through the right subclavian artery 3628. FIG. 36B shows an electrical lead path 3631 that runs through the left subclavian artery 3626. The lead paths 3630 and 3631 each represent a path in which a snare can be advanced to the blood pump assembly 3600 to capture and retrieve an electrical lead, or in which an electrical lead can be routed and connected to the blood pump assembly 3600. As show, the blood pump assembly 3600 can include an inflow cannula 3602, which can be positioned within the aortic valve and within the left ventricle (not shown). Imaging (e.g., fluoroscopy imaging) may be performed during the electrical lead retrieval or routing procedure assure proper navigation through the vasculature, including around the aortic arch 3617. The size of electrical lead wire may be small enough to fit within the left subclavian artery 3626 or right subclavian artery 3628. In some cases, the electrical lead wire has a size ranging from 3.5-18 Fr (French gauge). One advantage of such lead paths 3630/3631 is that such paths avoid transseptal routing of the electrical lead.

Figure 37A:
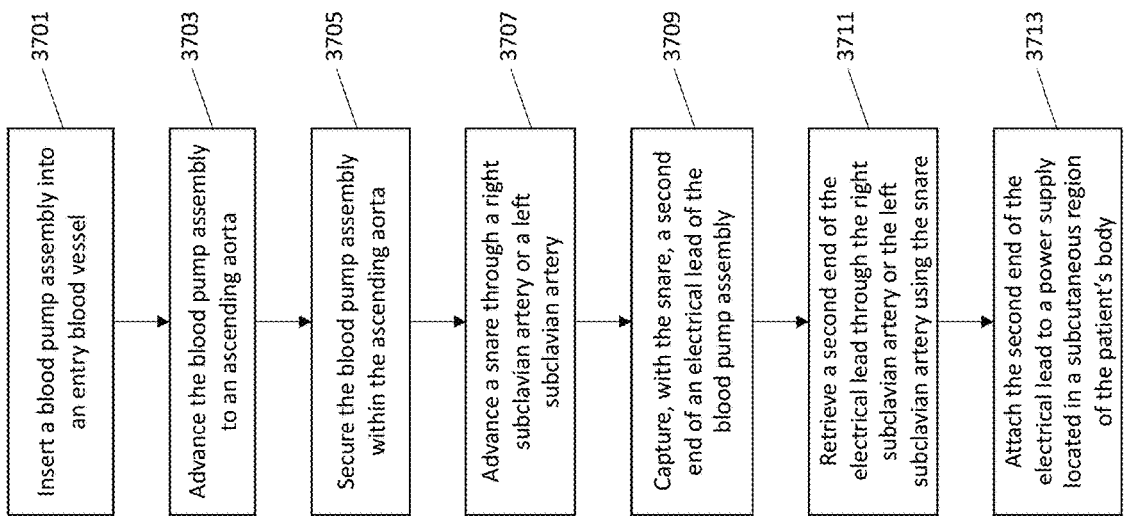
FIG. 37A is a flowchart indicating a method of implanting a blood pump assembly into an ascending aorta using a snare to retrieve an electrical lead.

FIG. 37A is a flowchart indicating a method of implanting a blood pump assembly into a patient's body. At 3701, the blood pump assembly is inserted into an entry blood vessel. In some cases, the entry blood vessel is the femoral artery. The blood pump assembly can include a blood pump having an inflow cannula and an electrical lead, as described herein. The electrical lead can have a first end electrically coupled to the blood pump. At 3703, the blood pump assembly is advanced through the entry blood vessel and to the ascending aorta of the patient. At 3705, the blood pump assembly is secured within the ascending aorta such that the inflow cannula is disposed through the aortic valve and within the left ventricle. Securing the blood pump assembly can include expanding one or more stents of the blood pump assembly such that the stent(s) contact the inner wall of the ascending aorta. At 3709, a snare is advanced through a right subclavian artery or a left subclavian artery of the patient. At 3711, a second end of the electrical lead is captured using the snare. At 3713, the second end of the electrical lead is electrically coupled to a power supply located in a subcutaneous region of the patient's body. In some cases, the power supply is located in a subclavicular region of the patient's body.

Figure 37B:
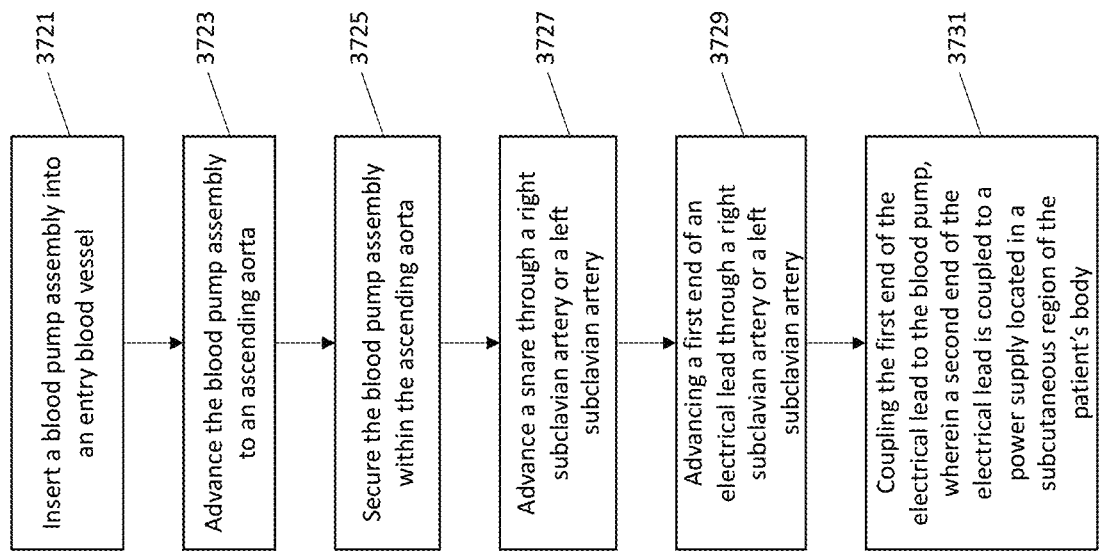
FIG. 37B is a flowchart indicating a method of implanting a blood pump assembly into an ascending aorta by routing an electrical lead to the blood pump assembly.

FIG. 37B is a flowchart indicating another method of implanting a blood pump assembly into a patient's body. At 3721, the blood pump assembly is inserted into an entry blood vessel. In some cases, the entry blood vessel is the femoral artery. The blood pump assembly can include a blood pump having an inflow cannula, as described herein. At 3723, the blood pump assembly is advanced through the entry blood vessel and to the ascending aorta of the patient. At 3725, the blood pump assembly is secured within the ascending aorta such that the inflow cannula is disposed through the aortic valve and within the left ventricle. Securing the blood pump assembly can include expanding one or more stents of the blood pump assembly such that the stent(s) contact the inner wall of the ascending aorta. At 3729, a first end of an electrical lead is advanced through a right subclavian artery or a left subclavian artery of the patient. At 3711, the first end of the electrical lead is electrically coupled to the blood pump. A second end of the electrical lead is coupled to a power supply located in a subcutaneous region of the patient's body. In some cases, the power supply is located in a subclavicular region of the patient's body.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A blood pump assembly, comprising:
a blood pump including a housing having one or more attachment portions;
a stent configured to transition from a collapsed configuration to an expanded configuration, the stent including a plurality of flexible segments that form a tubular wall defining an interior volume; and
one or more arms flexibly coupled to the stent or formed integrally with the stent, the one or more arms configured to removably couple to the one or more attachment portions of the blood pump to support the blood pump within the interior volume of the stent, wherein the one or more arms are configured to detach from the one or more attachment portions such that the blood pump is decoupled from the stent and is removable from the interior volume of the stent, wherein the one or more arms are configured to move out of a lumen of the stent and into or against the tubular wall of the stent when the blood pump is decoupled from the stent.

2. The blood pump assembly of claim 1, wherein the one or more attachment portions of the housing of the blood pump includes one or more slotted openings configured to capture one or more attachment members at distal ends of the one or more arms.

3. The blood pump assembly of claim 2, wherein the housing includes a magnetic material that is configured to magnetically couple with the one or more attachment members to retain the one or more arms within the one or more slotted openings.

4. The blood pump assembly of claim 2, wherein the blood pump housing includes a retention member associated with each of the one or more slotted openings, the retention member having a notch configured to accept a corresponding attachment member.

5. The blood pump assembly of claim 1, wherein the one or more arms are configured to bend radially inward with respect to the tubular wall of the stent to couple with the blood pump and support the blood pump within the interior volume of the stent.

6. The blood pump assembly of claim 1, wherein the one or more arms are configured to bend radially outward and form part of the tubular wall of the stent when detached from the blood pump.

7. The blood pump assembly of claim 6, wherein the one or more arms are made of a shape memory material having a pre-deformed shape that is in radial alignment with the tubular wall of the stent.

8. The blood pump assembly of claim 1, wherein the one or more arms are configured to detach from the one or more attachment portions upon translation of the blood pump with respect to the stent.

9. The blood pump assembly of claim 8, wherein upon translation, the one or more arms are configured to move radially outward and in alignment with the tubular wall of the stent.

10. The blood pump assembly of claim 1, wherein the blood pump includes a power supply configured to drive the blood pump.

11. The blood pump assembly of claim 1, further comprising a power supply separate from the blood pump, wherein the blood pump assembly further includes a second stent configured to support the power supply within an interior volume of the second stent, wherein the second stent includes a second set of one or more arms fixedly coupled to the second stent, and wherein the second set of one or more arms is configured to removably couple to a housing of the power supply.

12. The blood pump assembly of claim 11, wherein the power supply is electrically coupled to the blood pump by an electrical lead wire.

13. A method of implanting a blood pump assembly, the method comprising:
advancing the blood pump assembly through an entry blood vessel and to a target blood vessel, the blood pump assembly including:
a blood pump including a housing having one or more attachment portions; and a stent
including a plurality of flexible segments, the stent including two or more arms extending from an inner wall of the stent, the two or more arms detachably coupled to the one or more attachment portions of the blood pump, wherein the two or more arms are configured to move out of a lumen of the stent and into or against the inner wall of the stent when the blood pump is decoupled from the stent; and
expanding the stent within the target blood vessel such that the flexible segments contact an inner surface of the target blood vessel and form a tubular wall defining the inner wall of the stent, wherein the two or more arms support the blood pump within an interior volume of the stent.

14. The method of claim 13, further comprising percutaneously inserting a catheter containing the blood pump assembly in a collapsed configuration into the entry blood vessel.

15. The method of claim 13, wherein the entry blood vessel is a femoral artery, and the target blood vessel is an ascending aorta.

16. The method of claim 13, wherein one or more attachment members at distal ends of each of the two or more arms is captured within one or more slotted openings of the housing of the blood pump.

17. The method of claim 16, wherein each of the one or more attachment members is magnetically retained within a corresponding slotted opening by a magnetic material within the housing.

18. The method of claim 16, wherein each of the one or more attachment members is retained within a corresponding slotted opening by a retention member having a notch configured to accept the attachment member.

19. The method of claim 13, wherein the two or more arms are bent radially inward with respect to the tubular wall of the stent to couple with the blood pump and support the blood pump within the interior volume of the stent.

20. The method of claim 13, wherein the blood pump assembly includes a blood pump and a separate power supply, wherein expanding the stent includes:

expanding a first stent within the target blood vessel such that a first set of arms of the first stent supports the blood pump within an interior volume of the first stent, wherein the first set of arms is detachably coupled to first attachment portions of a housing of the blood pump; and expanding a second stent within the target blood vessel such that a second set of arms of the second stent supports the separate power supply within an interior volume of the second stent, wherein the second set of arms is detachably coupled to second attachment portions of a housing of the separate power supply.

21. The method of claim 20, wherein the separate power supply is electrically coupled to the blood pump by an electrical lead wire.

22. A method of removing a blood pump from a blood pump assembly implanted within a blood vessel, the method comprising:

advancing a retrieval sheath through the blood vessel toward the blood pump assembly, the blood pump assembly comprising:
the blood pump including a housing having one or more attachment portions; and
a stent including a plurality of flexible segments contacting an inner surface of the blood vessel and forming a tubular wall defining an interior volume, the stent including one or more arms extending from the tubular wall of the stent into the interior volume, the one or more arms detachably coupled to one or more attachment portions of the blood pump to support the blood pump within the interior volume of the stent;

detaching the blood pump from the stent by unlocking the one or more arms from the one or more attachment portions of the blood pump, wherein once the one or more arms are released from the one or more attachment portions, the one or more arms move radially outward in alignment with the plurality of flexible segments and out of the interior volume of the stent; and retrieving the blood pump out of the blood vessel using the retrieval sheath.

23. The method of claim 22, wherein unlocking the one or more arms comprises translating the blood pump relative to the stent to release an attachment member at a distal end of each of the one or more arms that is captured within a corresponding slotted opening of the housing of the blood pump forming an attachment portion of the one or more attachment portions.

24. The method of claim 23, wherein the attachment member is magnetically retained in the corresponding slotted opening by a magnetic material within the housing, wherein detaching the attachment member comprises overcoming a magnetic force retaining the attachment member.

25. The method of claim 22, wherein the blood pump is a blood pump or a power supply.

26. The method of claim 22, wherein the stent is left within the blood vessel after the blood pump is removed from the blood vessel.

27. The method of claim 26, further comprising advancing and deploying a second blood pump assembly within the blood vessel, the second blood pump assembly comprising a replacement blood pump supported within a second stent, wherein the second stent is expanded within the stent left within the blood vessel.

28. A method of implanting a blood pump assembly into a patient's body, comprising:

inserting, into an entry blood vessel, the blood pump assembly, the blood pump assembly including a blood pump having an inflow cannula and an electrical lead, the electrical lead having a first end coupled to the blood pump;

advancing the blood pump assembly through the entry blood vessel and to an ascending aorta of the patient;

securing the blood pump assembly within the ascending aorta such that the inflow cannula is disposed through an aortic valve and within a left ventricle;

advancing a snare through a right subclavian artery or a left subclavian artery of the patient; capturing, with the snare, a second end of the electrical lead;

retrieving the second end of the electrical lead through the right subclavian artery or the left subclavian artery using the snare; and attaching the second end of the electrical lead to a power supply located in a subcutaneous region of the patient's body.

29. The method of claim 28, wherein the power supply is located in a subclavicular region of the patient's body.

30. A method of implanting a blood pump assembly into a patient's body, comprising:

inserting, into an entry blood vessel, the blood pump assembly, the blood pump assembly including a blood pump having an inflow cannula;

advancing the blood pump assembly through the entry blood vessel and to an ascending aorta of the patient;

securing the blood pump assembly within the ascending aorta such that the inflow cannula is disposed through an aortic valve and within a left ventricle;

advancing a first end of an electrical lead through a right subclavian artery or a left subclavian artery; and coupling the first end of the electrical lead to the blood pump, wherein a second end of the electrical lead is configured to be coupled to a power supply located in a subcutaneous region of the patient's body.

31. The method of claim 30, wherein the power supply is located in a subclavicular region of the patient's body.

* * * * *